US007700758B2

(12) United States Patent
Tzertzinis et al.

(10) Patent No.: US 7,700,758 B2
(45) Date of Patent: Apr. 20, 2010

(54) METHODS AND COMPOSITIONS RELATING TO GENE SILENCING

(75) Inventors: George Tzertzinis, Cambridge, MA (US); George Feehery, West Newbury, MA (US); Christopher Noren, Boxford, MA (US); Corinna Tuckey, San Francisco, CA (US); Larry McReynolds, Beverly, MA (US); Yinhua Zhang, North Reading, MA (US)

(73) Assignee: New England Biolabs, Inc., Ipswich, MA (US)

( * ) Notice: Subject to any disclaimer, the term of this patent is extended or adjusted under 35 U.S.C. 154(b) by 1515 days.

(21) Appl. No.: 10/622,240

(22) Filed: Jul. 18, 2003

(65) Prior Publication Data

US 2004/0038278 A1 Feb. 26, 2004

Related U.S. Application Data

(60) Provisional application No. 60/402,769, filed on Aug. 12, 2002, provisional application No. 60/407,543, filed on Aug. 30, 2002, provisional application No. 60/467,541, filed on May 2, 2003.

(51) Int. Cl.
| C07N 21/04 | (2006.01) |
| C12Q 1/68 | (2006.01) |
| C12N 5/00 | (2006.01) |
| A61K 31/70 | (2006.01) |

(52) U.S. Cl. .................... 536/24.5; 435/6; 435/375; 514/44 A

(58) Field of Classification Search ................. None
See application file for complete search history.

(56) References Cited

U.S. PATENT DOCUMENTS

| 6,506,559 B1 | 1/2003 | Fire et al. | |
| 2002/0086356 A1 | 7/2002 | Tuschl | |
| 2002/0114784 A1 | 8/2002 | Li et al. | |
| 2002/0132346 A1 | 9/2002 | Cibelli | |
| 2002/0162126 A1* | 10/2002 | Beach et al. | .................. 800/8 |
| 2002/0173478 A1 | 11/2002 | Gewirtz | |
| 2003/0108923 A1 | 6/2003 | Tuschl et al. | |
| 2003/0125281 A1 | 7/2003 | Lewis et al. | |
| 2004/0014113 A1* | 1/2004 | Yang et al. | ..................... 435/6 |

FOREIGN PATENT DOCUMENTS

| AU | 3564702 | 6/2002 |
| EP | 1144623 | 8/2002 |
| NZ | 506648 | 8/2003 |
| WO | WO 99/32619 | 7/1999 |
| WO | WO 01/29058 | 4/2001 |
| WO | WO 01/36646 | 5/2001 |
| WO | WO 01/68836 | 9/2001 |
| WO | WO 01/75164 | 10/2001 |
| WO | WO 01/70949 | 6/2002 |
| WO | WO 02/055693 | 7/2002 |

OTHER PUBLICATIONS

Zamore et al., Cell, 2000, 101: 25-33.*
Ketting et al., Genes & Development, 2001, 15: 2654-2659.*
Gross et al., Nucleic Acids Research, 1987, 15: 431-442.*
EPO Search Report, Dec. 22, 2004.
Billy et al., PNAS 98/25:14428-14433 (2001).
Fire et al., "Potent and specific genetic interference by double-stranded RNA in *Caenorhabditis elegans*," Nature 391: 806-811 (1998).
Yang et al., "Specific Double-Stranded RNA Interference in Undifferentiated Mouse Embryonic Stem Cells," Mol. Cell. Biol. 21: 7807-7816 (2001).
Elbashir et al., "Duplexes of 21-nucleotide RNAs mediate RNA interference in cultured mammalian cells," Nature 411: 494-498 (2001).
Hammond et al., "Post-Transcriptional Gene Silencing by Double-Stranded RNA," Nature Reviews Genetics 2: 110-119 (2001).
Sharp, "RNA interference-2001," Genes & Dev. 15: 485-490 (2001).
Holen et al., "Positional effects of short interfering RNAs targeting the human coagulation trigger Tissue Factor," Nucleic Acids Res. 30: 1757-1766 (2002).
Donze and Picard, "RNA interference in mammalian cells using siRNAs synthesized with T7 RNA polymerase," Nucleic Acids Res. 30: No. 10 e46 (2002).

(Continued)

*Primary Examiner*—Ileana Popa
(74) *Attorney, Agent, or Firm*—Harriet M. Strimpel

(57) ABSTRACT

A method for obtaining a mixture of heterogenous short double-stranded RNA molecules suitable for use in gene silencing (hsiRNA) by subjecting large double-stranded RNA to enzymatic cleavage under specified conditions. The resulting mixture consistently includes enhanced representation of fragments having a size of 21-22 nucleotides absent any fractionation step. The fragments contain sequences that collectively span the entire length of the large double-stranded RNA from which they are derived. Double-stranded RNA with sequences that individually represent segments of a target mRNA may be analyzed using the methods described herein to identify the most active subset of hsiRNA fragments or individual siRNA fragments for achieving gene silencing for any gene or transcribed sequences. A method is additionally provided for preparing and cloning DNA encoding selected siRNA, hsiRNA mixtures or hairpin sequences to provide a continuous supply of a gene silencing reagent derived from any long double-stranded RNA.

18 Claims, 23 Drawing Sheets

OTHER PUBLICATIONS

Paddison et al., "Short hairpin RNAs (shRNAs) induce sequence-specific silencing in mammalian cells," Genes and Dev. 16:948-958 (2002).
Bernstein et al., "Role for a bidentate ribonuclease in the initiation step of RNA interference," Nature 409:363-366 (2001).
Paddison et al., "Stable suppression of gene expression by RNAi in mammalian cells," Proc. Natl. Acad. Sci. 99:1443-1448 (2002).
Myers et al., "Recombinant Dicer efficiently converts large dsRNAs into siRNAs suitable for gene silencing," Nature Biotechnology, 21:324-328 (2003).
Yang et al., "Short RNA duplexes produced by hydrolysis with Escherichia coli RNase III mediate effective RNA interference in mammalian cells," Proc. Natl. Acad. Sci. 99: 9942-9947 (2002).
Zhang et al., "Human Dicer preferentially cleaves dsRNAs at their termini without a requirement for ATP," EMBO Journal 21:5875-5885 (2002).
Amarzguioui et al., "Tolerance for mutations and chemical modifications in a siRNA," Nucleic Acids Res. 31:589-595 (2003).
Li et al., "Ribonuclease III cleavage of a bacteriophage T7 processing signal. Divalent cation specificity, and specific anion effects," Nucleic Acids Res. 21:1919-1925 (1993).
Zhang and Nicholson, "Regulation of ribonuclease III processing by double-helical sequence antideterminants," Proc. Natl. Acad. Sci. 94:13437-13441 (1997).
Nicholson, "Function, mechanism and regulation of bacterial ribonucleases," FEMS Microbiol. Reviews 23:371-390 (1999).
Sun and Nicholson, "Mechanism of Action of Escherichia coli Ribonuclease III. Stringent Chemical Requirement for the Glutamic Acid 117 Side Chain and $Mn^{2+}$ Rescue of the Glu117Asp Mutant," Biochem. 40:5102-5110 (2001).
Hannon, "RNA interference," Nature 418:244-251 (2002).
Elbashir et al., "RNA interference is mediated by 21- and 22-nucleotide RNAs," Genes & Dev. 15:188-200 (2001).
Martinez et al., "Single-Stranded Antisense siRNAs Guide Target RNA Cleavage in RNAi," Cell 110: 563-574 (2002).
Lee et al., "An Extensive Class of Small RNAs in Caenorhabditis elegans," Science 294: 862-864 (2001).
Elbashir et al., "Functional anatomy of siRNAs for mediating efficient RNAi in Drosophila melanogaster embryo lysate," EMBO Journal 20:6877-6888 (2001).
Milligan et al., "Oligoribonucleotide synthesis using T7 RNA polymerase and synthetic DNA templates," Nucleic Acids Res. 15:8783-8798 (1987).
Sun et al., "Intrinsic Double-Stranded-RNA Processing Activity of Escherichia coli Ribonuclease III Lacking the dsRNA-Binding Domain," Biochem. 40:14976-14984 (2001).
Robertson et al., "Purification and Properties of Ribonuclease III from Escherichia coli," Journal of Biol. Chem. 243:82-91 (1968).
Byron et al., "Inducing RNAi with siRNA Cocktails Generated by Rnase III," Ambion TechNotes Newsletter 10/1:4-7 (2003).
Zamore et al., "RNAi: Double-Stranded RNA Directs the ATP-Dependent Cleavage of mRNA at 21 to 23 Nucleotide Intervals," Cell 101:25-33 (2000).
Kawasaki et al., "siRNAs generated by recombinant human Dicer induce specific and significant but target site-independent gene silencing in human cells," Nucleic Acids Res. 31/3:981-987 (2003).
Ambros, "microRNAs: Tiny Regulators with Great Potential," Cell 107:823-826 (2001).
Court, Control of Messenger RNA Stability, Belasco, J.G. et al, eds, Academic Press, New York (1993) 71-116.
Sambrook et al., Molecular Cloning: A Laboratory Manual, $3^{rd}$ ed., Cold Spring Harbor Press, Cold Spring, NY: 7.75-7-81 (2001).

* cited by examiner

BglII-EcoRI malE fragment cloned in LITMUS 28i:

FIG. 4B-2

```
                                                                     23W ─────────────
                                                                       8W ────────────
         CCGCCAGTCCGAACAAAGAGCTGGCAAAAGAGTTCCTCGAAAACTATCTGCTGACTGATGAAGGTCTGGAAGCGG    525
                                                              25W ──────────→    ←──
                                                      30W ──────────→
                                                        19B ────────→
                                                         12B ───────→
                                                          17W ──────→
              ──────→
         ──────→      32W ──────────────────→
         TTAATAAAGACAAACCGCTGGGTGCCGTAGCGCTGAAGTCTTACGAGGAAGAGTTGGCGAAAGATCCACGTATTG    600
          ─────── 13B
                       5W ────────────→
                  10B,21B ─────────→
                        4W ──────→
                       29W ──────→
                35W ──────────→
          1B,9B ─────────→
         7B,11B ─────────→
         CCGCCACTATGGAAAACGCCCAGAAAGGTGAAATCATGCCGAACATCCCGCAGATGTCCGCTTTCTGGTATGCCG    675
                                                                  ←──────────
                                                                         36W ──────────→
         TGCGTACTGCGGTGATCAACGCCGCCAGCGGTCGTCAGACTGTCGATGAAGCCCTGAAAGACGCGCAGACTAATT    750
                ─────── 22B
                                                                  EcoRI
         CGAGCTCGAACAACAACAACAATAACAATAACAACAACCTCGGGATCGAGGGAAGGATTTCAGAATTCCTGCAGG    825
                         ←────────────────── 12W
         ATATCTGGATCCACGAAGCTTCCCATGGTGACGTCACCGGTTCTAGATACCTAGGTGAGCTCTGGTACCCTCTAG    900
              ←──────────────────── 33B                      ←──────── 32B

TCAAGGCC                                                                        908
```

FIG. 4C-1

NheI-BsrGI GFP fragment cloned in LITMUS 38i:

```
                                   19B─────────▶
          TAATACGACTCACTATAGGGGCCCGTGCAATTGAAGCCGGCTGGCGCCAAGCTTCTCTGCAGGATATCTGGATCC      75
3W,30W  NheI           24W,28W                          ◀─────────── 33W
          ACGAATTCGCTAGCCTACCGGTCGCCACCATGGTGAGCAAGGGCGAGGAGCTGTTCACCGGGGTGGTGCCCATCC     150

TGGTCGAGCTGGACGGCGACGTAAACGGCCACAAGTTCAGCGTGTCCGGCGAGGGCGAGGGCGATGCCACCTACG     225
                                                               ◀──────────── 13W
                                                                            18B─────
          GCAAGCTGACCCTGAAGTTCATCTGCACCACCGGCAAGCTGCCCGTGCCCTGGCCCACCCTCGTGACCACCCTGA     300
                                         ◀─────────── 15B
                                                  ◀─────────── 23B
                                                     ◀─────────── 20B
                                                          ◀─────────── 26W
                                                                   ◀───────────
                                                                         3B,25B ───
                                                                         34B,35B ──────
          ───────────────────▶       11W ──────────▶  6W,27W,31W ───────
          CCTACGGCGTGCAGTGCTTCAGCCGCTACCCCGACCACATGAAGCAGCACGACTTCTTCAAGTCCGCCATGCCCG     375
          ─── 5W
             ◀──────── 20W                                              36W ───────
                                                                21W ──────────
                                                 31B ──────────
                                                   9B ──────────
          ──────────────▶      12B ──────────
          ──────────────▶      10W ──────────
          ──────────────▶       5B ──────────
          AAGGCTACGTCCAGGAGCGCACCATCTTCTTCAAGGACGACGGCAACTACAAGACCCGCGCCGAGGTGAAGTTCG    450
```

FIG. 4C-2

```
                               10B
AGGGCGACACCCTGGTGAACCGCATCGAGCTGAAGGGCATCGACTTCAAGGAGGACGGCAACATCCTGGGGCACA    525

28B
                                                        14W
                                           24B
AGCTGGAGTACAACTACAACAGCCACAACGTCTATATCATGGCCGACAAGCAGAAGAACGGCATCAAGGTGAACT    600
— 17B
— 36B
                                                                1W,2W,4W,
                                                                8W,9W,12W,
                                                                25W,32W,1B
            33B                                   14B           27B,30B
TCAAGATCCGCCACAACATCGAGGACGGCAGCGTGCAGCTCGCCGACCACTACCAGCAGAACACCCCCATCGGCG    675

22W
                                              7W,22B
                                              23W
ACGGCCCCGTGCTGCTGCCCGACAACCACTACCTGAGCACCCAGTCCGCCCTGAGCAAAGACCCCAACGAGAAGC    750
                                        17W

21B     BsrGI
GCGATCACATGGTCCTGCTGGAGTTCGTGACCGCCGCCGGGATCACTCTCGGCATGGACGAGCTGTACAGGCATG    825
            16W                              13B
                                             16B

CGTCGACCCTCTAGTCAAGGCCTATAGTGAGTCGTATTACGGA    868
          18W
          6B
          19W
```

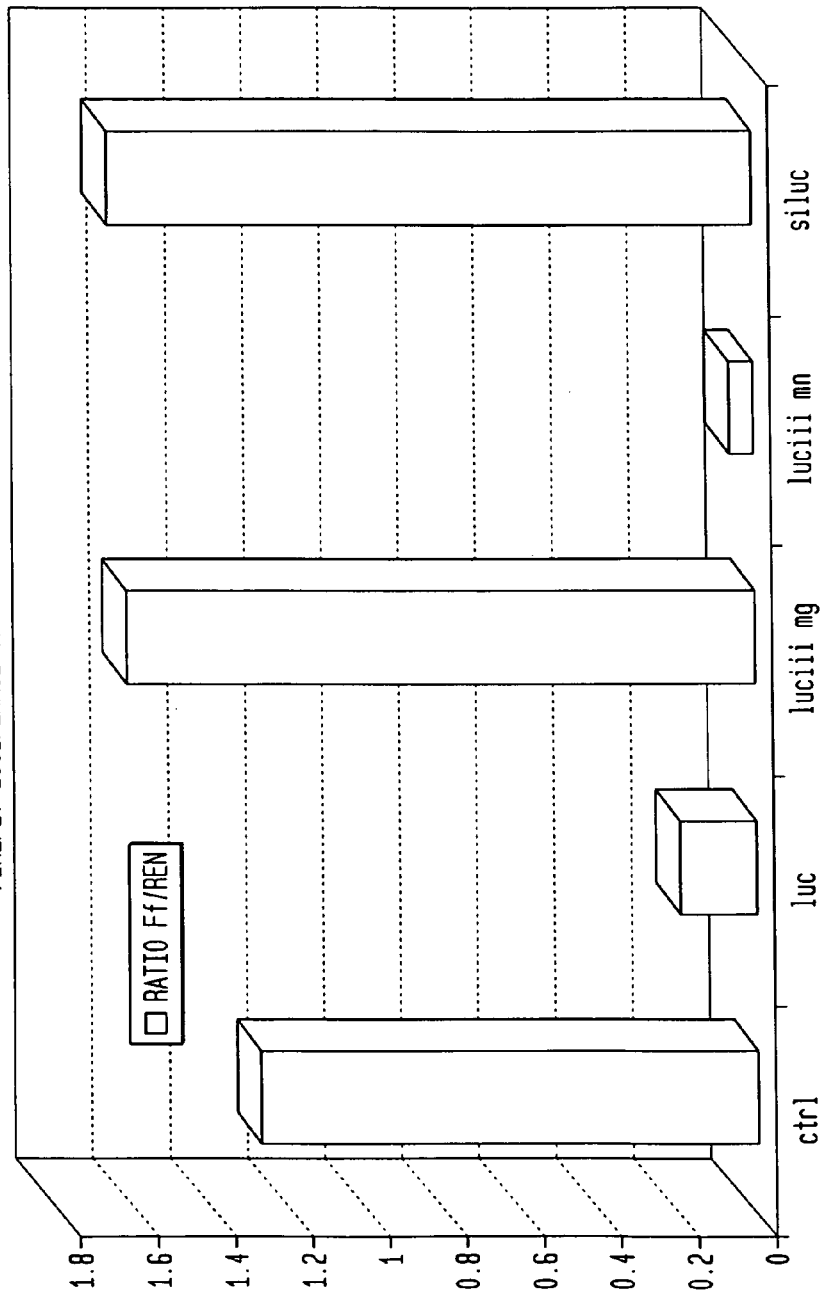

FIG. 6A — EGFP SILENCING IN HEK-293 CELLS
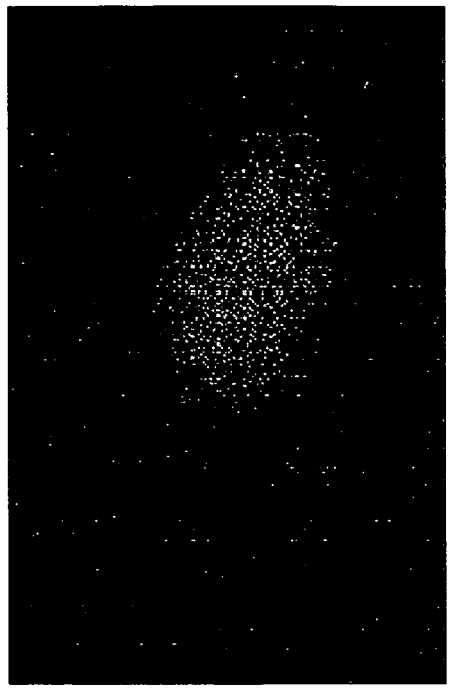
GFP dsRNA RNaseIII Mn$^{++}$
CONTROL

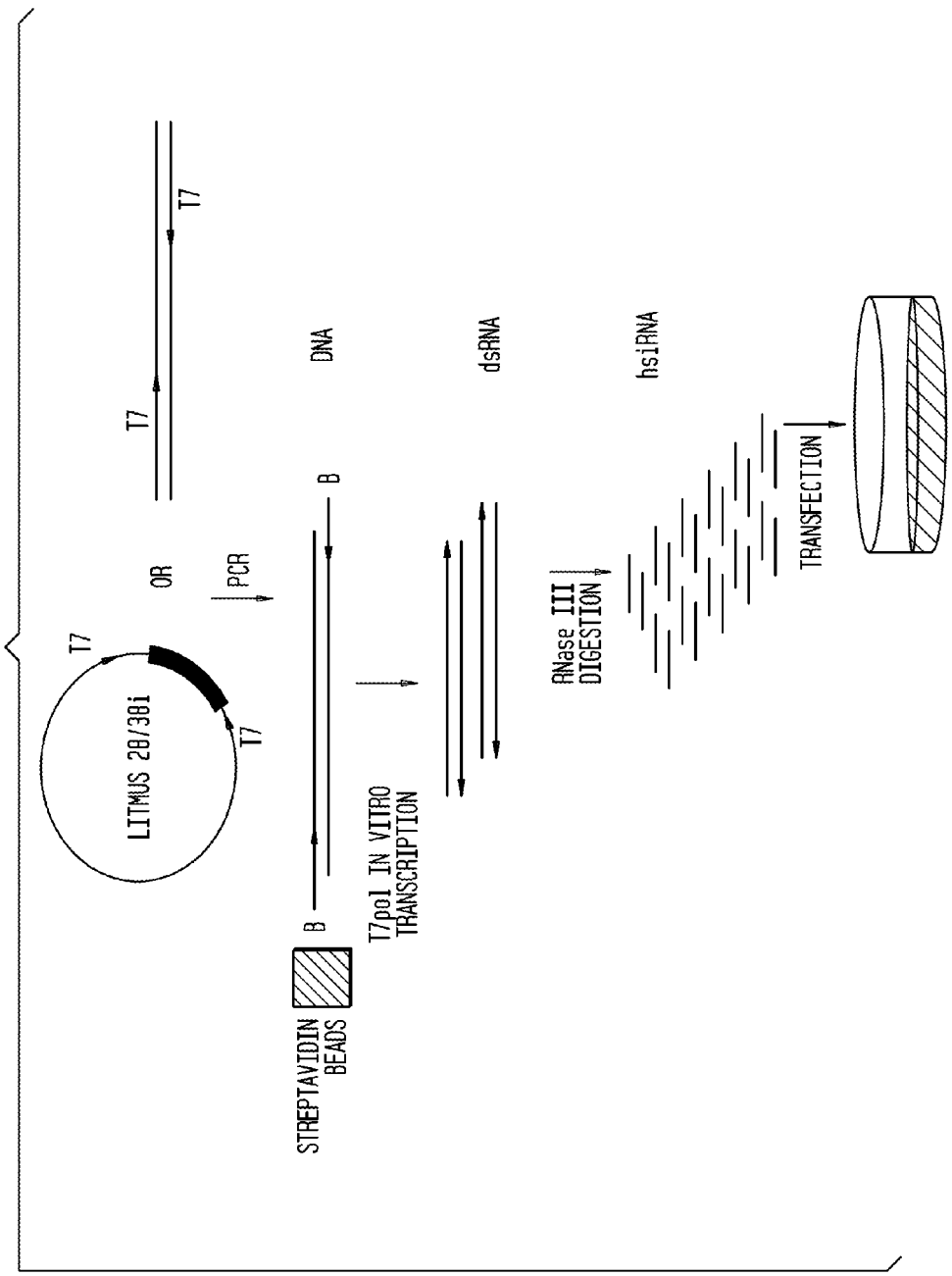

ANTI-DnMT1

ANTI-p53

METHODS AND COMPOSITIONS RELATING TO GENE SILENCING

CROSS REFERENCE

This Application gains priority from U.S. Provisional Application Ser. No. 60/402,769 filed Aug. 12, 2002, U.S. Provisional Application Ser. No. 60/407,543 filed Aug. 30, 2002 and U.S. Provisional Application Ser. No. 60/467,541 filed May 2, 2003. These Applications are herein incorporated by reference.

BACKGROUND OF THE INVENTION

RNA interference (RNAi) employing short double-stranded RNA (siRNA) is a powerful tool for silencing gene expression in mammalian cells (see for example, U.S. Pat. No. 6,506,559, International Publication No. WO 01/29058, International Publication No. WO 01/68836, International Publication No. WO 01/75164, U.S. Publication No. 20020114784, U.S. Publication No. 20030125281, U.S. Publication No. 2002162126, U.S. Publication No. 20030108923, U.S. Publication No. 20020173478, Fire, et al. *Nature* 391:806-811 (1998); Yang, et al., *Mol. Cell. Biol.* 21:7807-7816 (2001), Elbashir, et al., *Nature* 411:494-498 (2001), Hammond et al. *Nat. Rev. Genet* 2:110-119 (2001), Sharp, *Genes Dev.* 15:485-490 (2001)).

A standard method for generating siRNA relies on an inherently expensive chemical synthesis of a pre-determined short sequence. Because not all parts of a target sequence are equally effective in silencing, it is necessary to generate libraries of chemically synthesized fragments to identify those sequences which are effective (Holen et al. *Nucleic Acids Res.* 30:1757-1766, 2002)).

An alternative method for generating siRNA relies on in vitro transcription (see for example, Donze and Picard, *Nucleic Acids Res.* 30:1757-1766 (2002) and Paddison et al. *Genes and Dev.* 16:948-958 (2002)). While this approach does not require chemical synthesis it remains necessary to choose and test individual short sequences to determine which are most effective.

Several enzymatic approaches have been reported for cleaving double-stranded RNA molecules into short fragments. An evolutionarily conserved enzyme which is believed to cleave large dsRNA to produce siRNA in vivo has been identified as DICER. (Bernstein, et al., *Nature* 409:363-366 (2001)). This enzyme contains a helicase motif, a PAZ (PIWI-ARGONAUT-ZWILLE) domain and a tandem repeat of a catalytic domain which is RNaseIII-like. *Drosophila* extracts presumably containing DICER mixed with large dsRNA in vitro produce short dsRNA in a range of sizes. The preferred size for RNAi applications in this mixture was determined by Tuschl et al. to be 21-23 nucleotides (International Publication No. WO 01/75164). Problems associated with using crude cell extracts containing a putative cleavage enzyme are for example, that it is unclear what proteins in the mixture of proteins are necessary and sufficient to generate the observed effect. In addition, the extract is relatively inefficient at cleaving large double-stranded RNA with only a relatively small amount of the starting material being cleaved to the desired size in vitro even under extended incubation times. (Paddison et al., *Proc. Natl. Acad. Sci.* 99:1443 (2002)).

More recently, mammalian Dicer has been obtained recombinantly from baculovirus cell expression systems. Lysates of recombinant DICER produced in baculovirus infected insect cell cultures are reported to generate short double-stranded RNA fragments from large double-stranded RNA in the presence of a magnesium buffer. The purified siRNA fragments were used for "silencing" the expression of cognate genes in cultured mammalian cell lines (Myers et al. *Nature Biotechnology,* 21:324-328 (2003)). Limitations of this approach include the cost of baculovirus expression systems, the incomplete digestion of double-stranded RNA starting material and the need for gel based or other purification step to eliminate precursor RNA prior to performing silencing experiments.

An alternative enzymatic approach for generating small double-stranded RNAs has been to use *E. coli* RNaseIII in the presence of magnesium ions to partially digest large double-stranded RNA. (Yang et al. *Proc. Nat'l. Acad. Sci. USA* 99:9942-9947 (2002)). Problems associated with this approach include low recovery amounts of the double-stranded fragments in a specific size range larger than about 15 nt and the associated inconvenience of titration to avoid over or under-digestion. Unless digestion is carefully monitored, RNaseIII in the presence of magnesium ions cleaves large double-stranded RNA into very small fragments that are generally considered to have no known use in RNAi. Careful titration and timing of the partial digest at best yielded a smear throughout a gel after which, a particular size fraction could be recovered for use in RNA silencing in cultured mammalian cells (Yang, et al., *Proc. Nat'l. Acad. Sci. USA* 99:9942-9947 (2002)). A problem with this approach is the lack of certainty with respect to (a) an end product where the end product relates to yield of a dsRNA having a particular size larger than about 15 nucleotides and (b) the extent of representation of the large double-strand RNA sequence in the cleavage products. The latter may be important since not all parts of the sequence of a long double-stranded RNA are thought to be equally effective in gene silencing and important sequences may be under-represented while unimportant sequences may be over-represented.

Because gene silencing has become a methodology of great importance in understanding molecular functions in cells and organisms, it is desirable to have a rapid, cost effective and reliable method for generating double-stranded RNA suitable for silencing of any gene.

SUMMARY OF THE INVENTION

In an embodiment of the invention, a method is provided for producing a heterogeneous siRNA (hsiRNA) mixture, that includes digesting a preparation of large double-stranded RNA in a reaction mixture containing a divalent transition metal cation and RNaseIII. Digestion of large double-stranded RNA with RNAseIII in the presence of transition metal ions can be achieved at a w/w ratio in a range of about 0.005:1 to 25:1 of RNAseIII to large double-stranded RNA. More particularly, the w/w ratio may be in the range of about 0.0125:1 to 10:1. Examples of transition metal cations for use in making hsiRNA mixtures include manganese, nickel, cobalt, zinc and cadmium. A suitable concentration of divalent transition metal ions is from about 5-100 mM. While the concentration is not critical, 10-20 mM manganese ions is a preferred range. The production of hsiRNA may be achieved in less than about 6 hours and preferably in less than about 2 hours, or more preferably less than 1 hour or as little as about 5 seconds.

In an embodiment of the invention, a method for producing an hsiRNA mixture is provided which includes digesting a preparation of large double-stranded RNA in a reaction mixture containing RNaseIII at a ratio of enzyme to substrate (w/w) being greater than or equal to about 0.25:1

In an embodiment of the invention, methods of silencing or reducing expression of one or more target gene includes introducing into a host cell, an hsiRNA mixture capable of silencing or reducing expression of the target genes. Accordingly, the hsiRNA can be prepared by (a) digesting a preparation of large double-stranded RNA in a reaction mixture containing a divalent transition metal cation and RNaseIII, or (b) digesting a preparation of large double-stranded RNA in a reaction mixture containing RNaseIII in a ratio of enzyme to substrate (w/w) being greater than or equal to about 0.25:1. A set of heterogeneous double-stranded RNA fragments can be introduced into the host cell where the fragments have overlapping sequences and have a size of about 15-30 bases, the set of hsiRNA having sequences that represent a substantial portion of the sequence of the large double-stranded RNA from which they are derived by in vitro enzymatic cleavage with RNaseIII. In the above methods, the large dsRNA has a nucleotide sequence that is complementary to all or part of the target gene or mRNA.

In an embodiment of the invention, a set of double-stranded RNA fragments is provided that includes a plurality of overlapping fragments of a size of about 15-30 nucleotides, the overlapping fragments representing a substantial portion of the sequence of one or more large double-stranded RNA from which they are derived by in vitro enzymatic cleavage where the enzyme is preferably purified. One strand of the large double-stranded RNA characteristically has a sequence complementary to part or all of a target messenger RNA. Preferably, a substantial percentage, for example, at least about 50% of the fragments in the set are in the size range of 21-22 nucleotides prior to any gel purification step.

The substantial portion of the sequence of the large double-stranded RNA represented by the set of double-stranded RNA fragments may be more than about 50% or preferably more than about 65%. In addition, more than 30% of the set of RNA fragments may have a fragment size of about 18-25 base pairs. At least one fragment in the set, but as many as at least about 50%, or 75% or indeed 100% of the fragments in the set may be capable of causing cleavage of the target mRNA. The set of fragments may additionally be capable of gene silencing when introduced into a eukaryotic cell.

In an additional embodiment of the invention, a method is provided for creating a library of DNA clones, each clone corresponding to one or more double-stranded RNA fragments from an hsiRNA mixture. The method includes the steps of (a) denaturing the hsiRNA mixture to form a mixture of unpaired RNA strands; (b) ligating to a 3' end of the unpaired RNA strand, a first single-strand DNA primer and to a 5' end of the unpaired RNA strand, a second single-strand DNA primer; (c) reverse transcribing the chimeric DNA-RNA products to form complementary DNA fragments; (d) synthesizing double-stranded DNA from the reversed transcribed DNA-RNA product using the second single-strand primer to synthesize the second strand or amplifying the DNA-RNA product using polymerase dependent amplification methods; and (e) inserting one or more DNA fragments into a vector to form the library of DNA clones. The embodiment optionally includes the steps of enzymatically removing the 5'phosphate from each strand prior to the first ligation step and enzymatically phosphorylating the 5'end of the product of the first primer ligation prior to ligation of the second primer.

The 5' end of the RNA strand in step (b) above may be dephosphorylated and the 3' end of the RNA strand in step (b) above may have a 3' hydroxyl end. The first DNA primer described above may have both a 5' and a 3' phosphate and be ligated to the 3' end prior to ligation of a second primer to the 5' end. In addition, the RNA strand ligated to the first primer may be subsequently phosphorylated and then ligated to the second primer. The second primer in this reaction may be non-phosphorylated on the 3' end. The vectors utilized in the above methods may be pUC19 or a Litmus vector. However, any vector suitable for cloning DNA fragments can be used including those for expression in eukaryotic cells.

The DNA clones produced by the above methods may be used to reduce expression of one or more target genes in a eukaryotic cell. Reducing expression of a target gene in a cell or organism provides a means of analyzing a resulting phenotypic change either in the cell or in tissues containing the cell or in an organism as a whole. Understanding the role of gene expression in a phenotype can provide insights into mechanism of disease and methods of treating diseases and for diagnosis. It can also provide a means to enhance a desired characteristic in the organism. Altering gene expression by gene silencing using DNA clones or mixtures of hsiRNA described above can provide valuable tools for analyzing a biochemical pathway in which the gene product functions and can be used in conjunction with other reagents such as antibodies.

The availability of DNA clones as described above provides an opportunity to make transgenic non-human animals in which a particular target gene expression is altered by the presence of the recombinant DNA for expressing a particular siRNA fragment.

In an embodiment of the invention, a kit is provided for preparing an hsiRNA mixture, that includes a preparation of RNaseIII, and an RNase buffer containing manganese ions in the range of about 5 mM-100 mM and optionally reagents for synthesizing a large double-stranded RNA.

In an embodiment of the invention, a method is provided for obtaining a large double-stranded RNA molecule, that includes (a) inserting a DNA fragment or library of DNA fragments encoding a double-stranded RNA into a vector having cloning sites flanked by opposing promoters e.g., T7 promoters; (b) performing in vitro or in vivo transcription; and (c) obtaining the large double-stranded RNA molecule.

In an embodiment of the invention, a rapid discovery method is provided for identifying an hsiRNA mixture which is capable of increased gene silencing of a target gene and includes: (a) synthesizing a plurality of large dsRNAs each large dsRNA having a sequence complementary to a segment of a target gene; (b) digesting each of the large dsRNA with RNaseIII in the presence of a manganese ions to produce a corresponding hsiRNA mixture; (c) introducing each hsiRNA mixture into a eukaryotic cell to determine whether gene silencing occurs; and (d) determining which of the hsiRNA mixtures caused increased gene silencing. Gene silencing may be further enhanced by combining a pre-selected hsiRNA mixture with a selected second hsiRNA mixture or by combining individual siRNA fragments selected from the hsiRNA mixtures or subsets thereof on the basis of silencing activity. These fragments can then be combined to form a novel mixture of desired gene silencing activity.

In an embodiment of the invention, a method is provided for identifying a sequence corresponding to an siRNA from a cleavage site in a mRNA, that includes: (a) obtaining an hsiRNA mixture enzymatically; (b) introducing the hsiRNA into a cell; (c) extracting cleaved mRNA from the cell; (d) determining the sequence of terminal nucleotides at the cleavage site of the siRNA cleaved mRNA; and (e) identifying the siRNA sequence from the cleavage site sequence and neighboring nucleotides from the intact mRNA. This method may be utilized to obtain a set of siRNA fragments that include double-stranded RNA of about 15-30 nucleotides that bind specifically to mRNA to initiate cleavage of the mRNA.

A 20 µl reaction mixture of 400 bp dsRNA (0.25 µg) corresponding to human PKR, E. coli RNaseIII (final concentration 0.05 µg/µl) and 5, 10, 20 or 50 mM manganese chloride buffer (lanes 2-5) or 10 mM magnesium chloride containing buffer (lane 6) was incubated for 20 minutes at 37° C. The digestion products were analyzed on a 20% TBE-acrylamide gel. Substantially greater amounts of 20-25 bp fragments were obtained in the presence of all concentrations of manganese ions than is observed in the presence of magnesium ions.

Figure 1A:
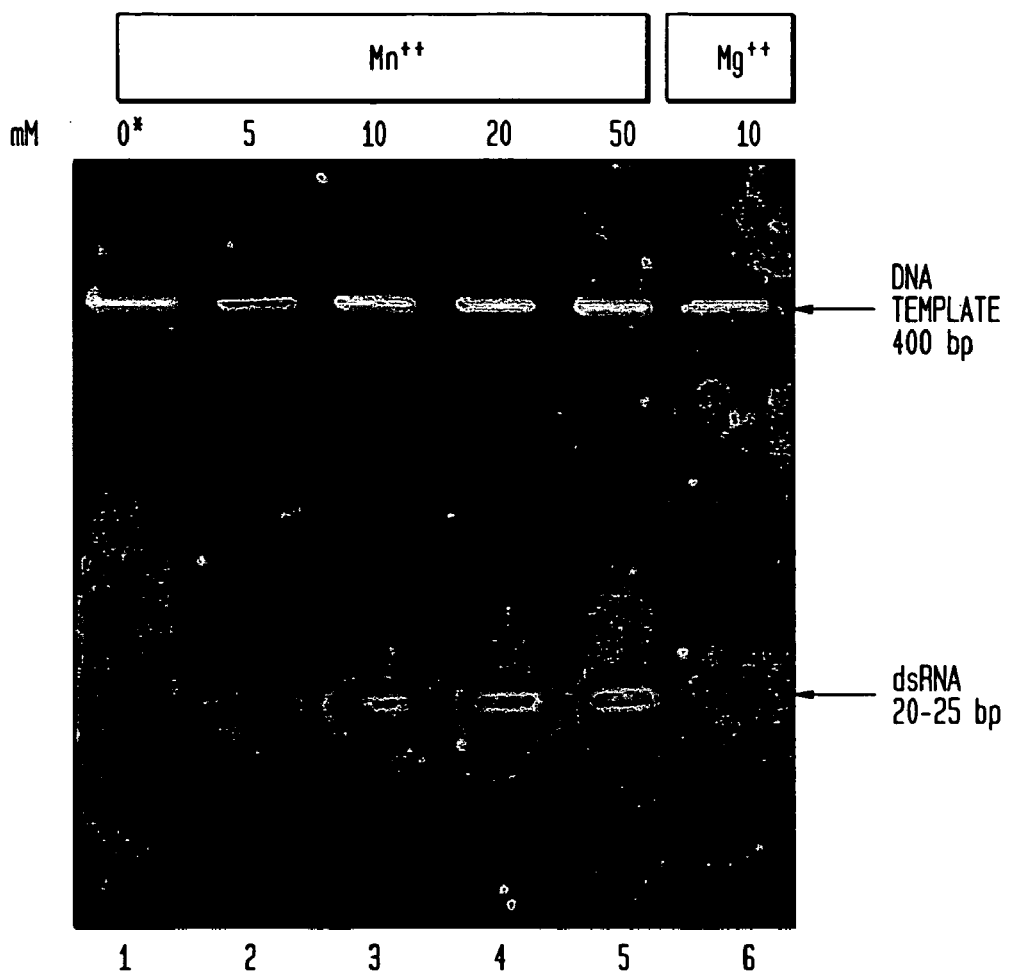
FIG. 1A shows the effect of $Mn^{2+}$ ion concentration on the production of an hsiRNA mixture.
Figure 1B:
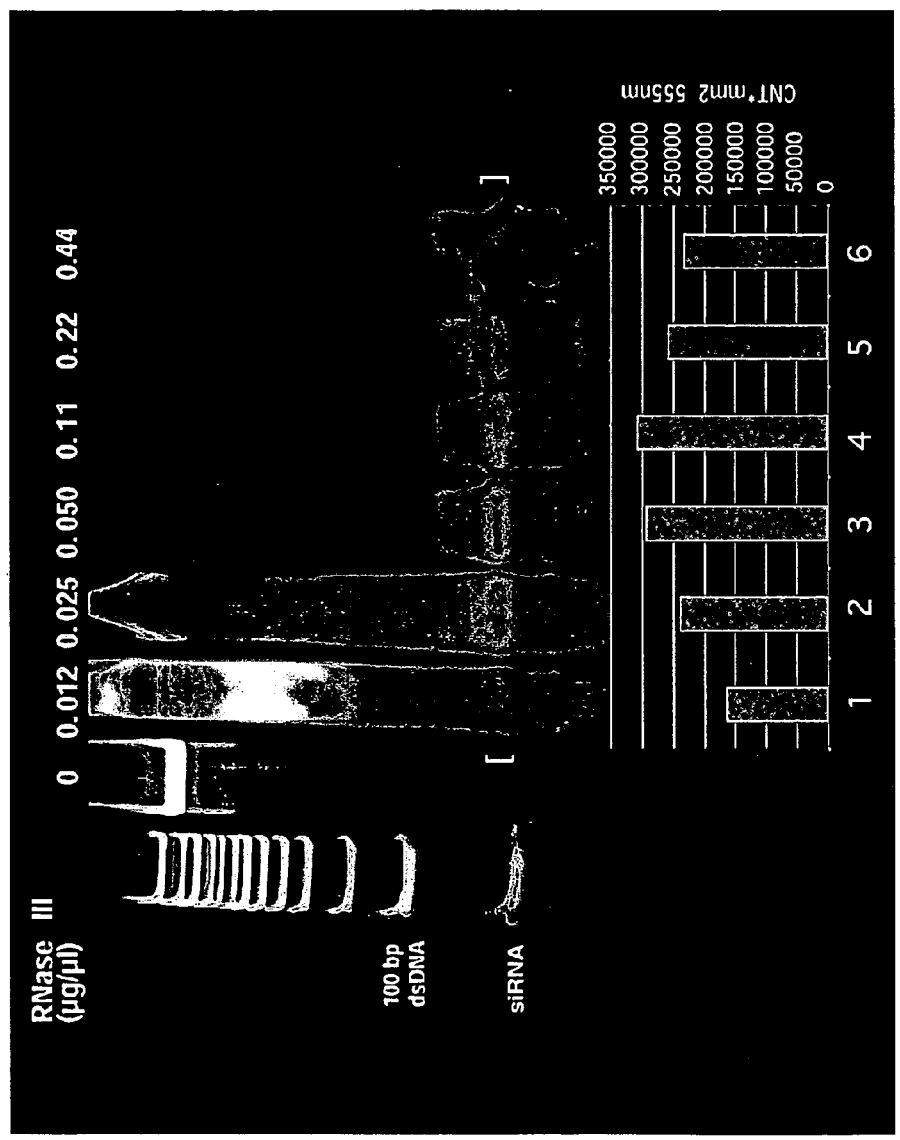

FIG. 1B shows the effect of varying concentrations of RNaseIII on formation of an hsiRNA mixture in 20 mM $Mn^{2+}$ buffer.

50 µl reaction mixtures containing 1000 bp dsRNA (2.5 µg) corresponding to firefly luciferase and 0, 0.5, 1, 2, 4, 8 and 16 µl of RNaseIII (1.36 mg/ml) were digested for 20 minutes at 37° C. After the reaction was terminated, 40 µL of each sample was analyzed on 20% native PAGE. The amount of the hsiRNA mixture in the size range of 20-25 base pairs (bracketed) was determined using fluorescence densitometry of the ethidium bromide stained gel as shown in the histogram (fluorescence intensity X area). 4 µL of RNaseIII (1.36 mg/mL) was sufficient to produce a substantial fraction of fragments in the desired size range.

Figure 1C:

FIG. 1C shows how the optimal ratio of RNaseIII to substrate was determined for the efficient production of an hsiRNA mixture using variable amounts of RNaseIII with a fixed amount of substrate.

50 µl reaction mixtures containing 1000 bp dsRNA (0.56 ug) corresponding to C. elegans chitin synthase was digested with a variable amount of RNaseIII. The RNaseIII/substrate w/w ratio of 1.7, 0.8, 0.4 and 0.2 was calculated for lanes 2-5 respectively. The cleavage buffer contained 10 mM $MnCl_2$. The amount of enzyme in 50 µl for each sample in lanes 2-9 was 0.1, 0.05, 0.025, 0.012, 0.006, 0.003, 0.0015, 0.0007 µg/µl. Lane 1 contains a double-stranded DNA marker and lane 10 contains no enzyme.

Figure 1D:
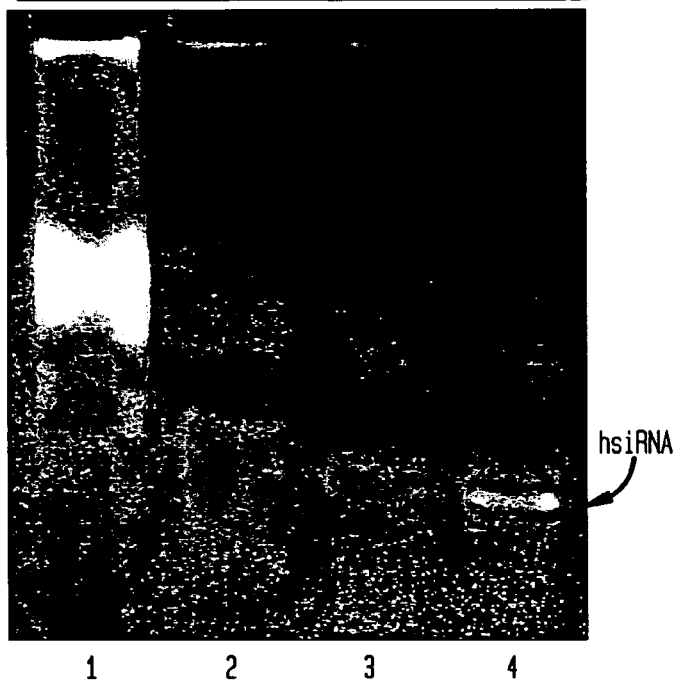

FIG. 1D shows how the optimal ratio of RNaseIII to substrate can be determined for the efficient production of hsiRNA mixture using a fixed amount of RNaseIII and variable amounts of substrate.

50 µl reaction mixtures containing RNaseIII at 0.1 µg/µl and a variable amount of the chitin synthase double-stranded RNA where the concentration of substrate in lanes 1-4 is 0.69 µg/µL, 0.37 µg/µL, 0.17 µg/µL and 0.06 µg/µL and the ratio of RNaseIII to substrate (w/w) is 0.2, 0.4, 0.8 and 1.7 respectively.

Figure 1E:
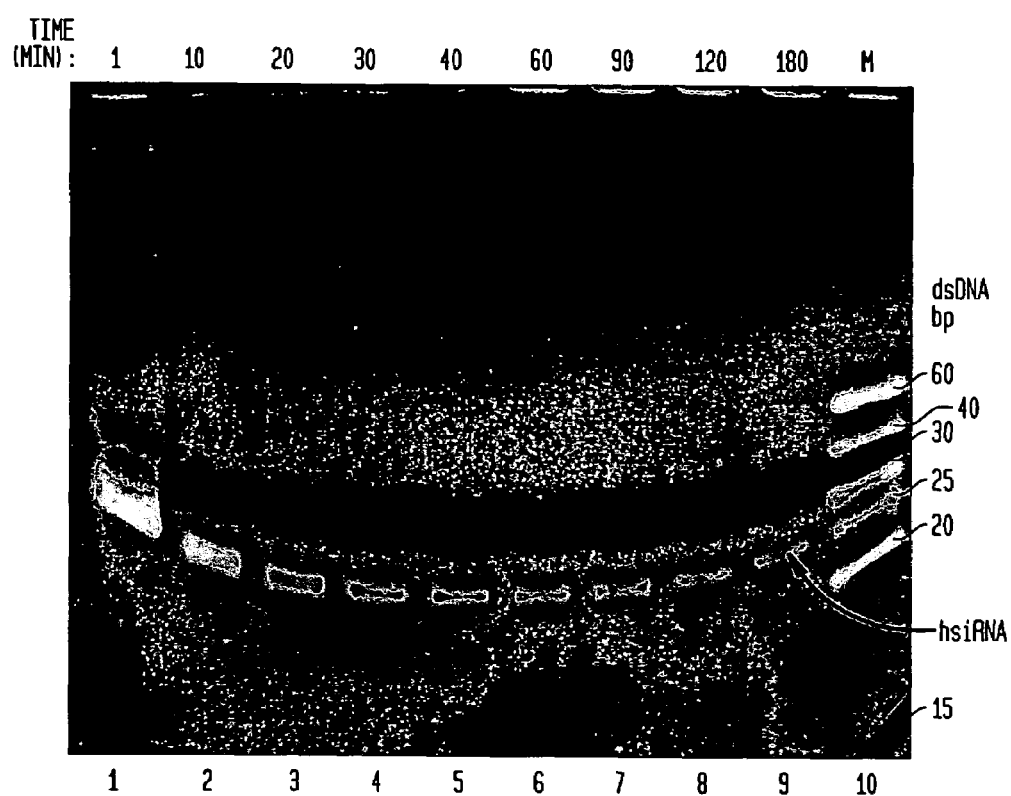

FIG. 1E shows the effect of time of incubation on the formation of hsiRNA mixtures in the presence of 10 mM manganese ions. 5.6 µg dsRNA (1000 bp) were digested with 10 µg total RNaseIII in 100 µl. Each lane contains $\frac{1}{10}^{th}$ of the reaction taken at 1, 10, 20, 30, 40, 60, 90, 120 and 180 minutes (lanes 1-9). Lane 10 contains a dsDNA marker.

Figure 1F:
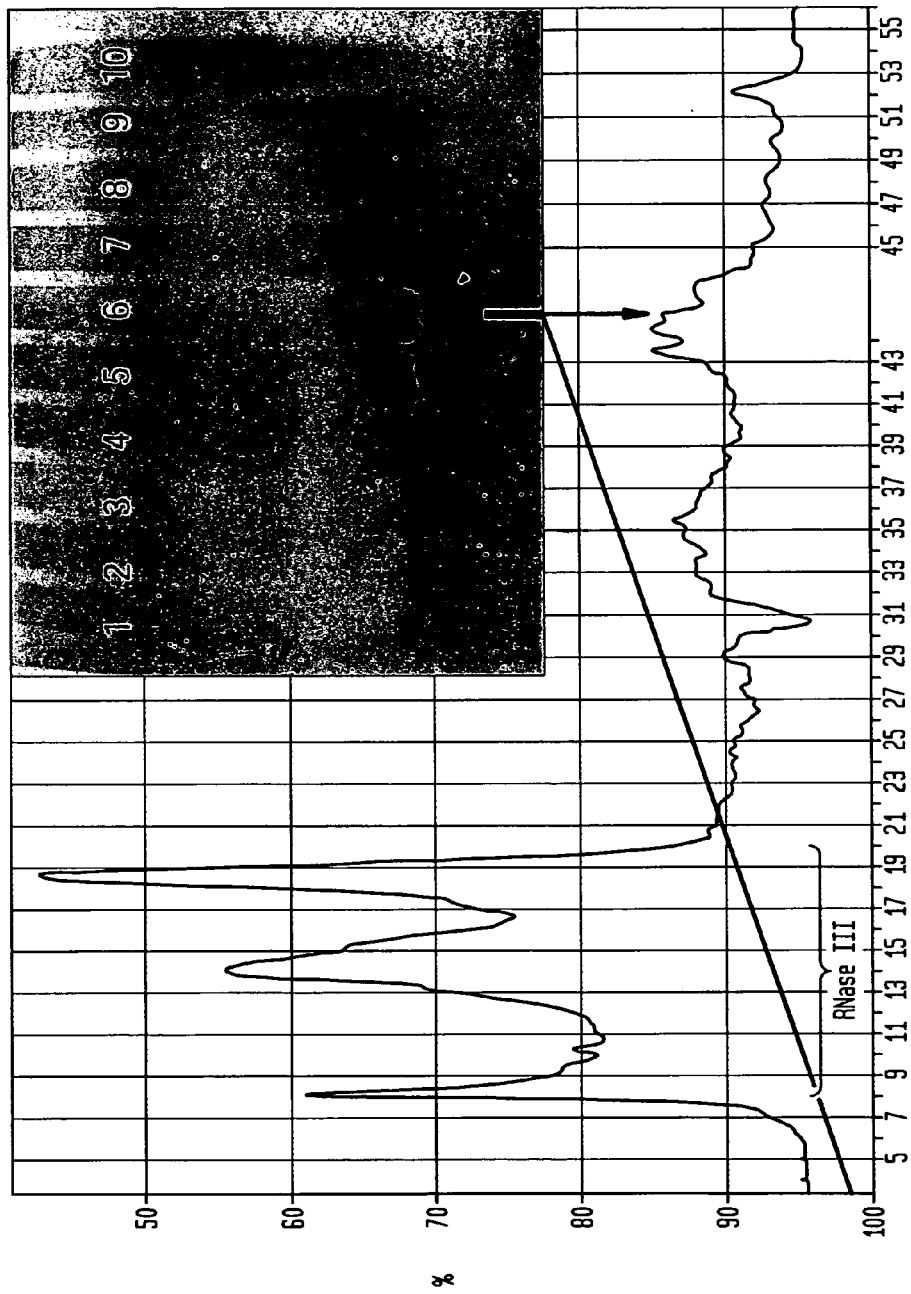

FIG. 1F shows the purification of hsiRNA on a Pharmacia Q Sepharose HP anion exchange column. 1 mg of CREB dsRNA (800 bp) was digested with 1 mg of RNaseIII, in 50 mM Tris-HCl, pH 7.5, 20 mM $MnCl_2$ 1 mM dithiothreitol for 20 minutes at 37° C. The digested sample was directly loaded on a 1 ml Q Sepharose HP column, washed with 5 ml of 10 mM Tris-HCl, ph 7.5 (Buffer A) and eluted with a 0-2.0 M NaCl gradient in Buffer A. Flow rate used was 2 ml/minute. RNaseIII elute from the column between 0.025-0.2 M NaCl. Lanes 1-10 shows the elution profile of the hsiRNA from the column with the arrow (Lane 6) corresponding to the location on the gradient (0.40-0.45 M NaCl) where the predominant ~18-25 bases hsiRNA elutes.

Figure 2:
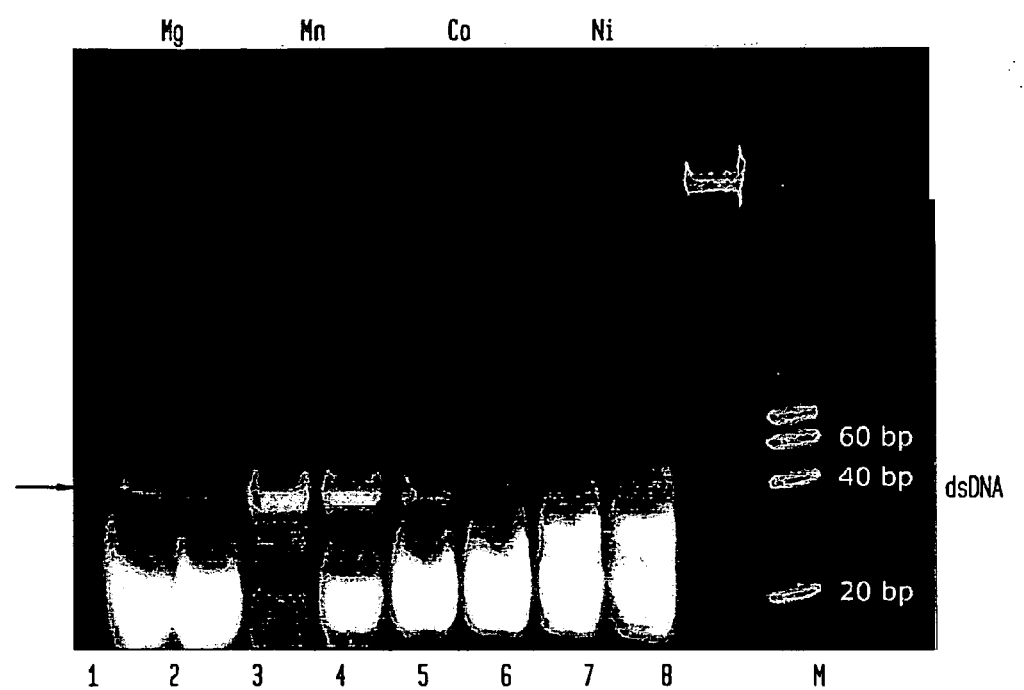

FIG. 2 shows the effect of $Mg^{2+}$, $Mn^{2+}$, $Co^{2+}$, and $Ni^{2+}$ on RNaseIII digestion on GFP dsRNA (800 bp).

Each reaction mixture contains 1 µg GFP double-stranded RNA in 50 µl buffer final volume, supplemented with metal ions to 10 mM final concentration: $Mg^{2+}$ (lanes 1 and 2), $Mn^{2+}$ (lanes 3 and 4), $Co^{2+}$ (lanes 5 and 6), $Ni^{2+}$ (lanes 7 and 8) and using a concentration of 0.04 µg/µl and 0.02 µg/µl RNaseIII for each metal ion respectively. Lane 9 has full length GFP dsRNA. Lane M contain Markers are 20, 40, 60, 80 bp long dsDNA.

Figure 3A:
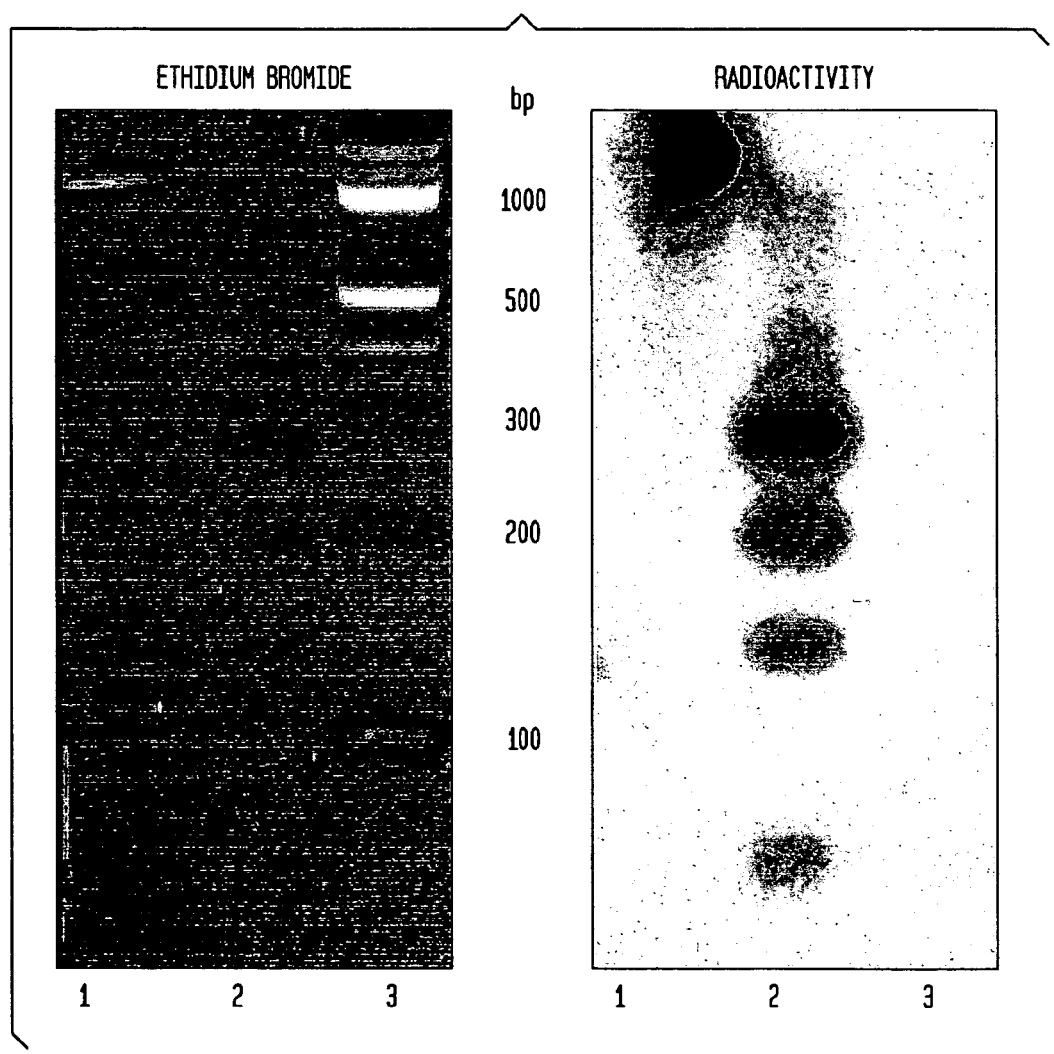

FIG. 3A shows the correlation of DNA fragments detected by intercalating dye (left) and probe with radiolabeled hsiRNA fragments from dsRNA corresponding to the DNA substrate.

p53 DNA fragment was used as a template for generating an hsiRNA mixture as described in Example VII. Lane 1 shows undigested DNA; lane 2 shows DNA digested with AciI; and lane 3 shows a 100 base ladder marker. DNA samples were run on an agarose gel and stained with ethidium bromide (left panel), then transferred to a membrane according to Example III. The DNA was probed with the gel purified labeled hsiRNA mixture (right panel).

Figure 3B:
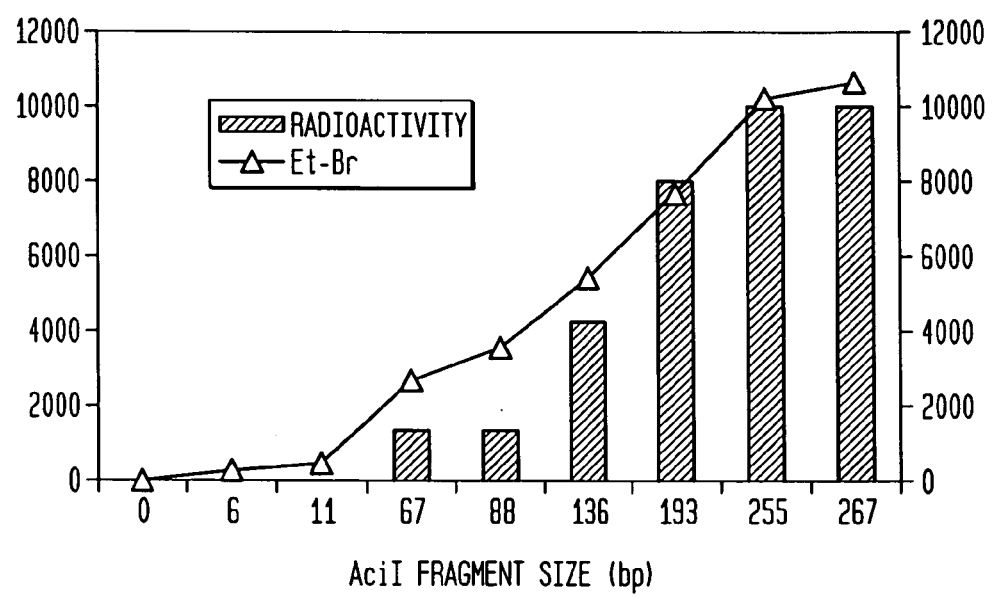

FIG. 3B shows a quantitative analysis of the ethidium fluorescence (line) and radioactivity (bar graph) of the bands in lane 2 in FIG. 3A. The intensity of the bands on the stained and radioactive gels correspond to the predicted signal based on fragment size. The signal in the Southern blot shows that the radioactive hsiRNA are representative of the entire length of the parent RNA.

Figures 1, 4A:
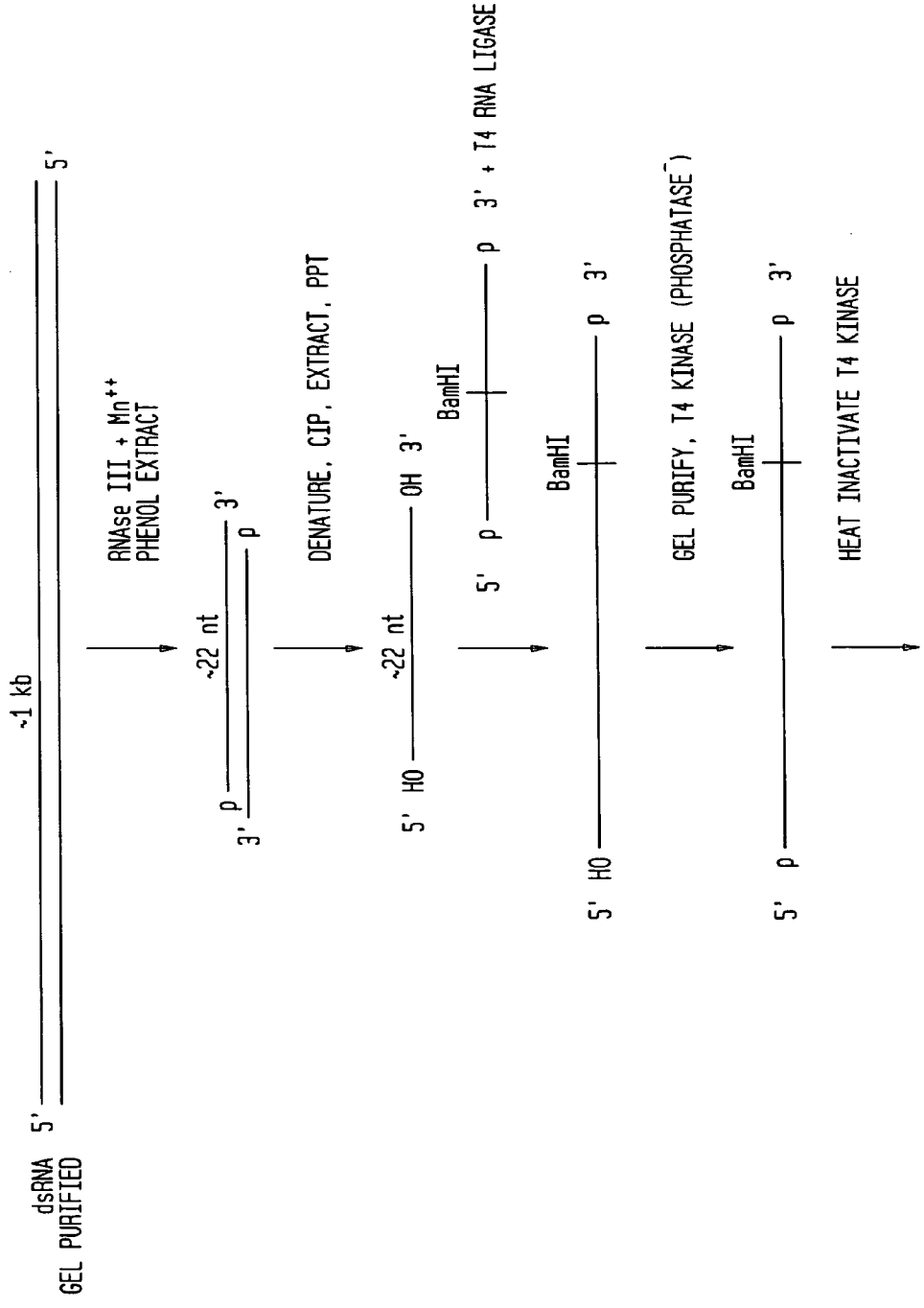
Figures 2, 4A:
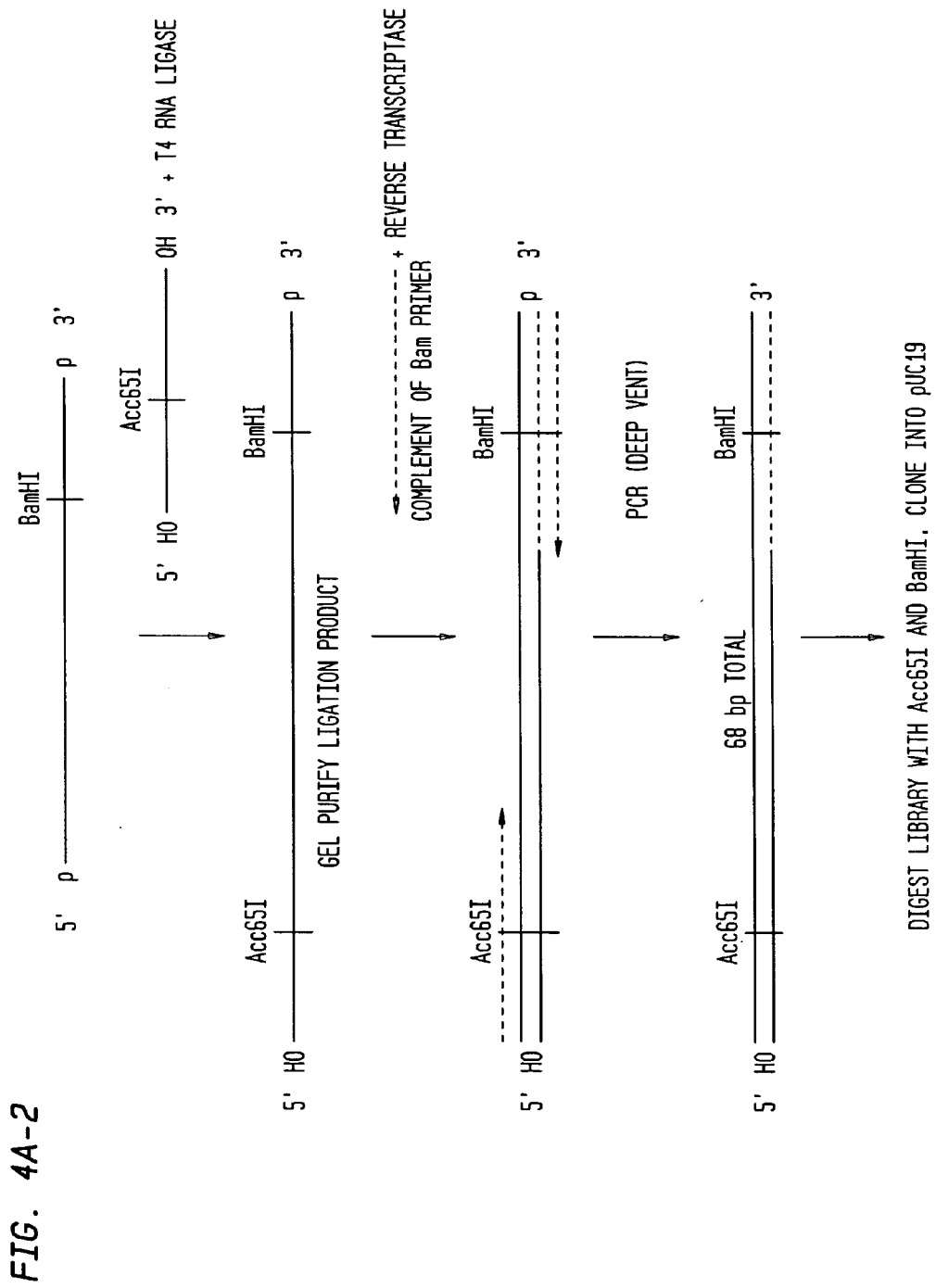

FIG. 4A is a schematic showing a method for cloning RNaseIII digestion products.

Figures 1, 4B:
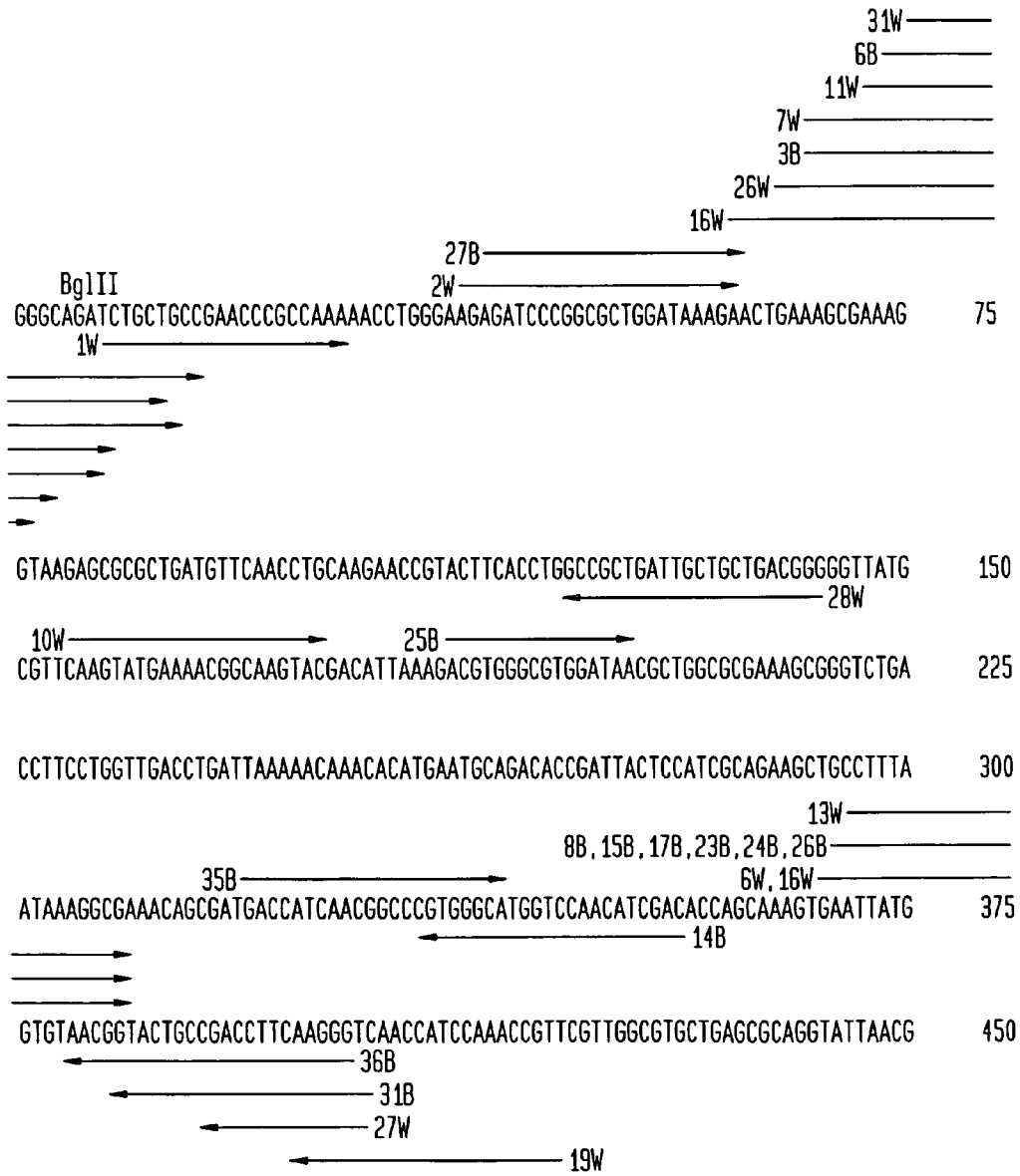

FIG. 4B is a sequence (SEQ ID NO:1) of the malE transcript with flanking Litmus 28i polylinker sequence enclosed by the opposing T7 promoters (Table 1). Restriction sites originally used to clone malE into Litmus are marked. Arrows correspond to sequences cloned as shown in FIG. 4A; the direction of the arrowhead indicates whether the sequence corresponds to the sequence shown (left to right) or the complementary strand (right to left).

FIG. 4C is a sequence (SEQ ID NO:2) of the GFP transcript with flanking Litmus 28i polylinker sequence enclosed by the opposing T7 promoters. Restriction sites originally used to clone GFP into Litmus are marked. Arrows correspond to sequences cloned as shown in FIG. 4A; the corresponds to the sequence shown (left to right) or the complementary strand (right to left).

Figure 4D:
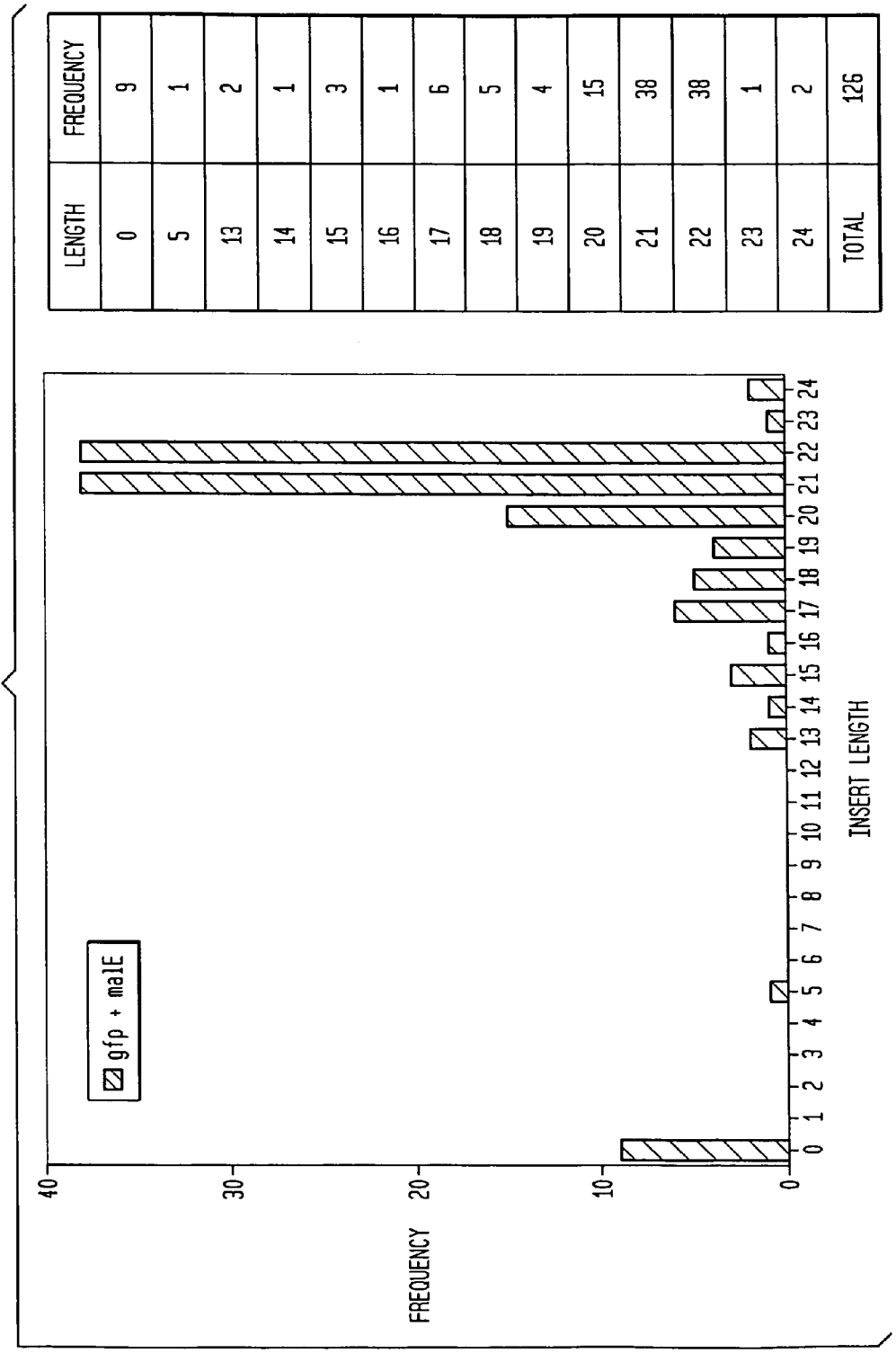

FIG. 4D is a summary in the form of a histogram and a table reporting the insert lengths in individual DNA clones. The numbers are compiled from the analysis of total clones from both malE and GFP. The y axis represents numbers of clones while the x-axis describes the insert length.

FIG. 5 shows that transfection of Drosophila cells with a Ffluc hsiRNA mixture (Example VI) substantially silences GL-2 Firefly luciferase while the RNaseIII product formed in the presence of $Mg^{2+}$ and in the absence of $Mn^{2+}$ is ineffective.

Specific targeted gene silencing was demonstrated by comparing the luminescence of extracts from Drosophila cells expressing both firefly luciferase and Renilla luciferase after transfection with the hsiRNA mixtures for firefly luciferase. The comparison is represented in a histogram expressing the ratio in RLU of firefly luciferase luminescence to Renilla luciferase. Shown in the histogram are: control cells which were not transfected with any form of double-stranded RNA fragment (ctrl); undigested double-stranded RNA corresponding to luciferase (luc: 1.2 kb); Ffluc double-stranded RNA after cleavage with RNAseIII in the presence of magnesium ions (luciii mg), cells transfected with Ffluc hsiRNA (luciii mn) and 22 bp chemically synthesized siRNA for GL3 luciferase (siluc).

FIG. 6A shows that a GFP hsiRNA mixture effectively silences green fluorescent protein (GFP) expression in HEK-293 cells using fluorescence microscopy. (i) control in which cells have been transfected with a plasmid containing GFP cDNA; and (ii) cells transfected with a plasmid containing GFP cDNA and hsiRNA corresponding to GFP (Example III).

Figure 6B:
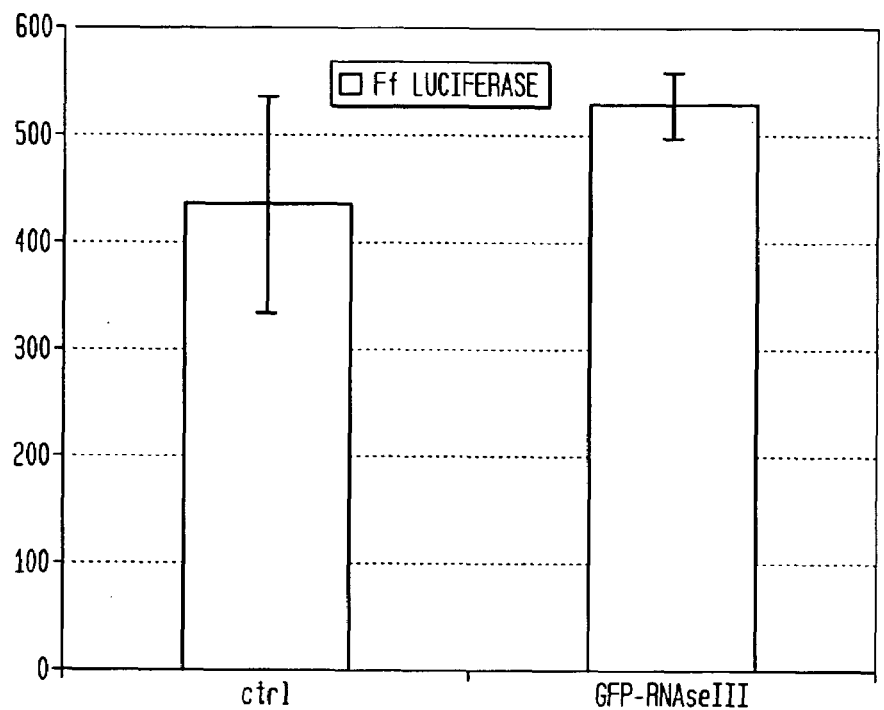

FIG. 6B shows that gene silencing is specific for the hsiRNA used. The amount of luciferase in HEK-293 cells was measured by luminescence (RLU), both cells not transfected with double-stranded RNA (ctrl) and cells transfected with an hsiRNA mixture derived from GFP double-stranded RNA (GFP-RNAsesIII) showed no observed effect on luciferase activity.

Figure 6C:
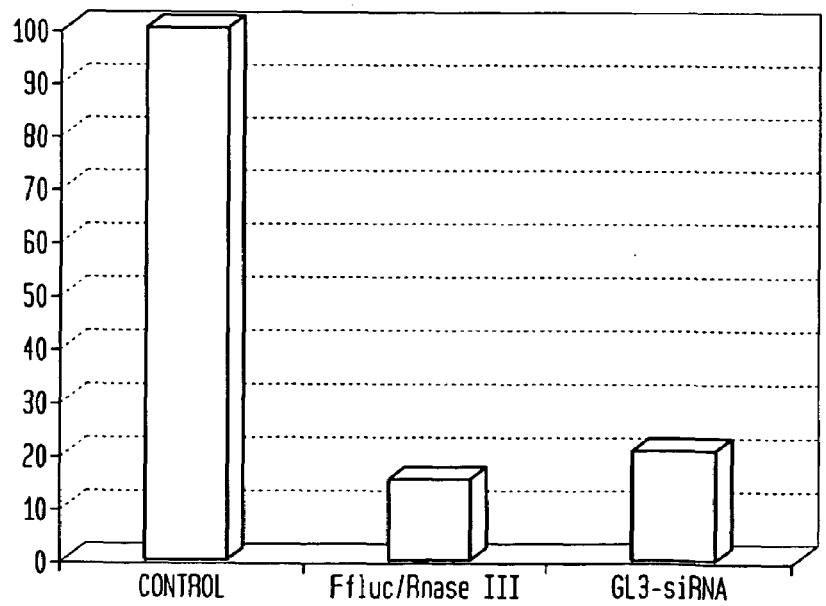

FIG. 6C shows that an hsiRNA mixture silences luciferase as effectively as synthetic hsiRNA. Luciferase in HEK-293 cells was measured by luminescence (RLU). Cells not transfected with double-stranded RNA (ctrl); transfected with an hsiRNA mixture derived from firefly luciferase double-stranded RNA (Ffluc-hsiRNase); transfected with synthetic siRNA for GL3-luciferase (GL3-siRNA). Both the hsiRNA mixture and siRNA resulted in targeted silencing of luciferase.

Figures 7A, 7B, 7C:
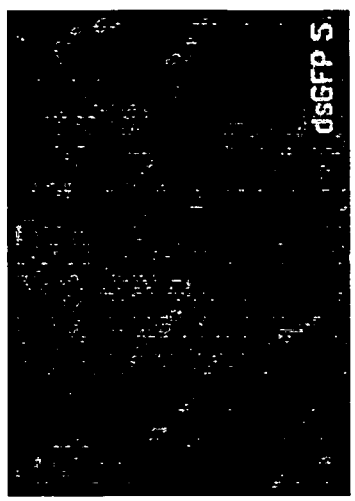
Figure 7E:
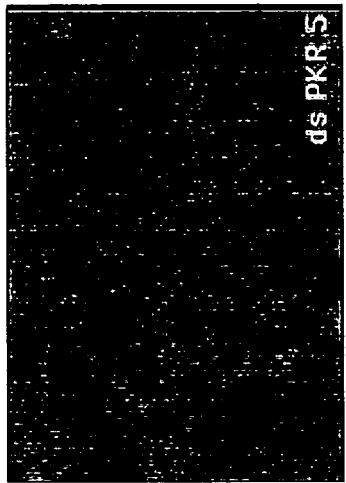
Figure 7D:
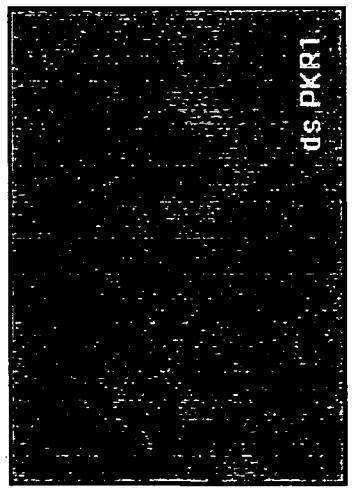

FIG. 7 shows the potency of targeted silencing using GFP hsiRNAs in COS-7 cells. Fluorescence microscopy shows gene silencing in cells transfected with a plasmid expressing GFP together with 6 ng (b) and 30 ng of GFP hsiRNA (c) and no detectable gene silencing in control cells (not transfected with double-stranded RNA) (a), 5 ng of PKR (d) or 30 ng of PKR hsiRNA (e).

Figure 8A:
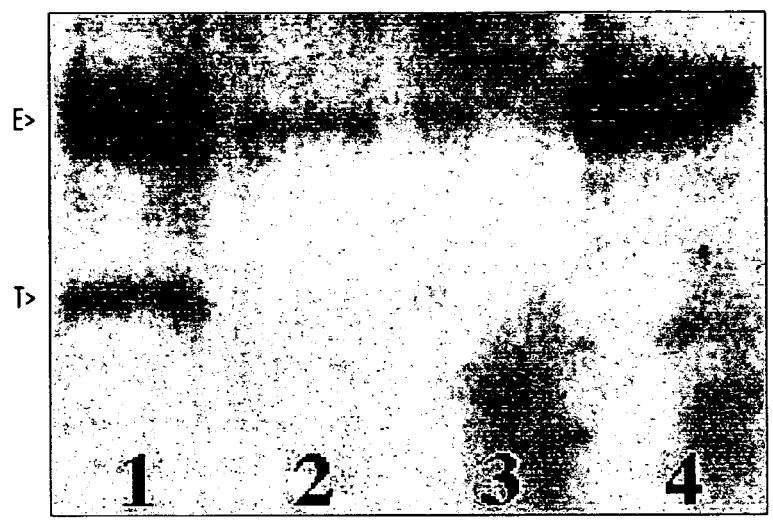
Figure 8B:
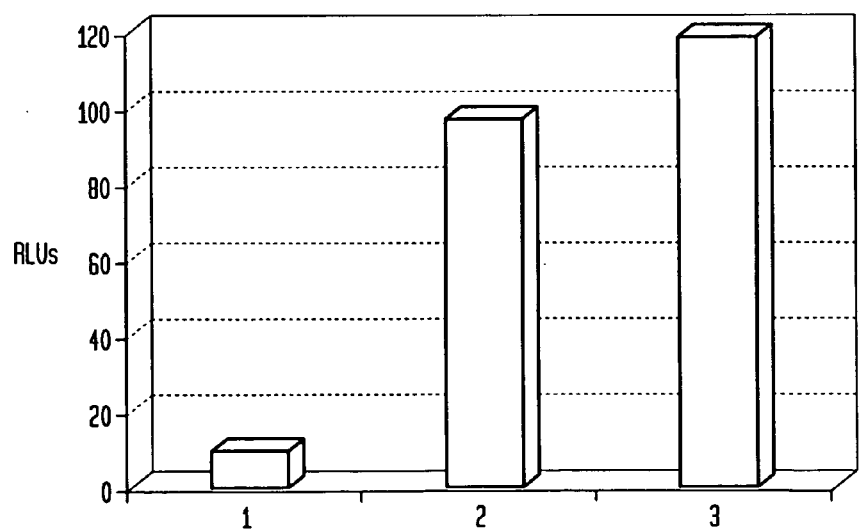

FIGS. 8A and 8B shows the targeted silencing of endogenous monkey and transfected human p53 expression in monkey COS-7 cells after transfection with a human p53 hsiRNA mixture or a Rluc-hsiRNA mixture. Cos-7 cells were simultaneously transfected with a plasmid expressing Renilla luciferase (Rluc).

FIG. 8A shows a western blot of cell extracts with anti-p53 antibody. E> denotes the position of endogenous p53 and T> the position of a transfected p53 fragment (amino acids 100-353). The Western blot reflects the amount of transfected and endogenous p53 expression in cells: after transfection with 50 ng Rluc-hsiRNA (lane 1); after transfection with 50 ng of a human p53 hsiRNA mixture (lane 2); after transfection with 100 ng of a human p53 hsiRNA mixture (lane 3); and in the absence of transfection (lane 4).

FIG. 8B shows that Rluc-hsiRNA silences Renilla luciferase in the transfected cells shown in FIG. 8A while a p53-hsiRNA mixture has no effect on expression of luciferase. Histogram bars labeled 1, 2 and 3 relate to samples analyzed in lanes 1, 2 and 3 in FIG. 6A here measuring expression levels of Renilla luciferase in (RLU). The histogram shows that a Rluc-hsiRNA mixture silences expression of luciferase but not hup53 in lane 1 and a p53-hsiRNA mixture which is effective in hup53 in lane 1 and a p53-hsiRNA mixture which is effective in silencing endogenous and human p53 in lane 2 and has no apparent silencing effect on Renilla luciferase.

FIG. 9 is a schematic representation of a kit for making any desired large dsRNA for cleavage with RNAseIII in the presence of manganese so as to form an hsiRNA mixture for transfection into cells for gene silencing studies.

Figure 10A:
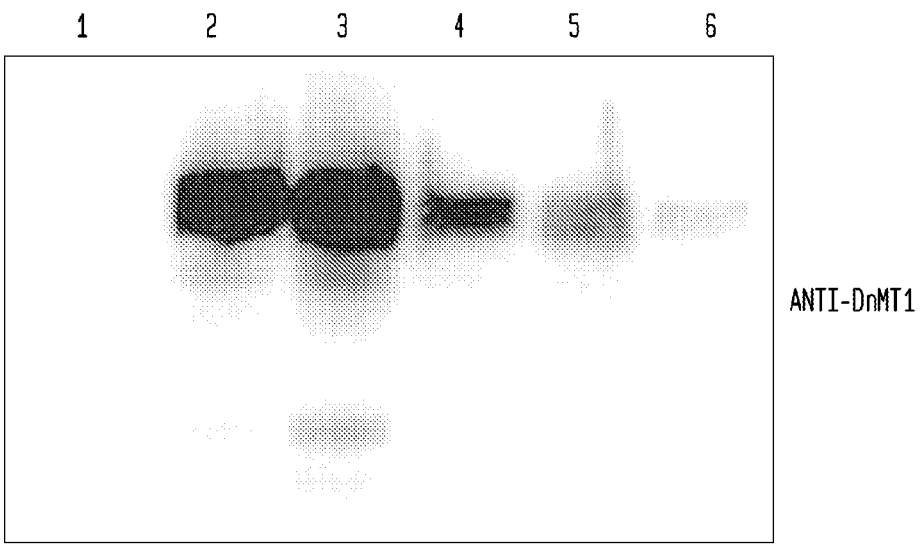

FIG. 10a is a Western Blot with anti-DnMt1 antibody which shows the knock down effect on DnMT1 of three mixtures of hsiRNA where each mixture corresponds to a different segment of DnMT1. The knockdown effect is detectable by the decrease or absence of the corresponding protein band.

Lane 1 contains an extract from untransfected cells;

Lane 2 contains an extract from cells transfected with a plasmid expressing DnMT1;

Lane 3 contains an extract from cells transfected with a plasmid expressing DnMT1 and with 100 ng siRNA corresponding to luciferase;

Lane 4 contains an extract from cells transfected with a plasmid expressing DnMT1 and with 100 ng hsiRNA from Dnmt1 segment 1;

Lane 5 contains an extract from cells transfected with a plasmid expressing DnMT1 and with 100 ng hsiRNA from DnMt1 segment 3;

Lane 6 contains an extract from cells transfected with a plasmid expressing DnMT1 and with 100 ng hsiRNA from Dnmt1 segment 2.

Figure 10B:
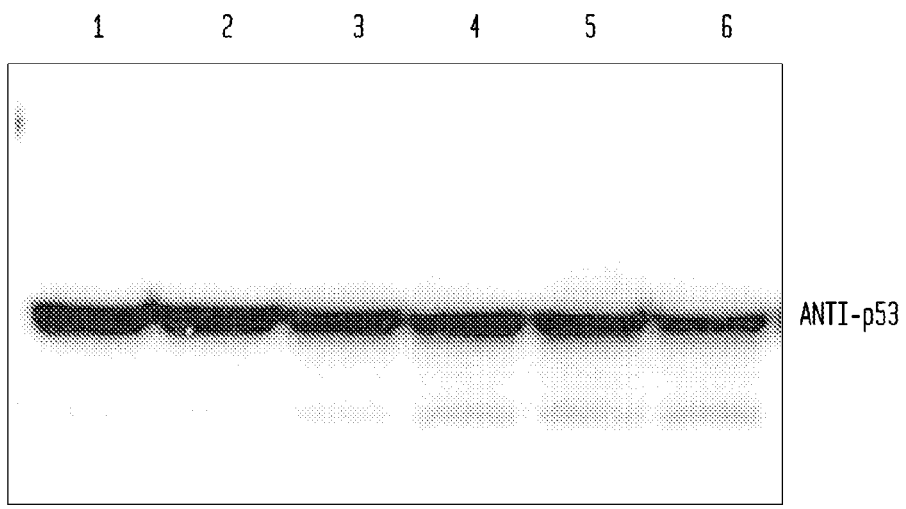

FIG. 10B is a Western blot with anti-p53 antibody which shows the absence of knockdown effect on the expression of p53 in the presence of the three mixtures shown in FIG. 10A. Lanes 1-6 contain extracts as described for FIG. 10A.

FIG. 11 is a schematic representation of a protocol for identifying a siRNA induced cleavage site in a target mRNA.

(a) a target mRNA of known sequence which is subjected to an hsiRNA mixture obtained by RNaseIII cleavage of a large dsRNA in the presence of 20 mM manganese ions.

(b) cleaved mRNA fragments (c) labeled extension DNA primers and products (d) primer extension products analyzed on a sequence gel.

DESCRIPTION OF THE EMBODIMENTS

A heterogeneous mixture of short double-stranded (ds) RNA fragments containing overlapping sequences that represent a substantial portion of a large dsRNA and which are effective in silencing gene expression has been achieved using RNaseIII in the presence of buffers that contain manganese or other divalent transition metal ions and/or high ratios of enzyme to substrate.

The enzymatic approach to generating short dsRNA for gene silencing from large dsRNA is desirable over synthetic chemical approaches. However, DICER extracts or recombinant DICER are only available in low amounts and cleave relatively inefficiently in vitro. Additionally, the mechanism by which DICER cleaves RNA may yield a mixture less rich in potential siRNAs for silencing (Zhang et al. *EMBO J.* 21:5875-5885 (2002) Amarzguioui, et al., *Nucleic Acids Res.* 31:589-595 (2003)).

In contrast, RNaseIII which is readily produced in large amounts and is very active, rapidly cleaves large dsRNA into fragments that are ineffective for gene silencing.

The enzymatic properties of RNaseIII have been studied for reasons other than for gene silencing. Among these experiments, some substituted magnesium in the enzyme buffer with other divalent cations. It was however concluded that such substitution was less desirable for RNaseIII activity than magnesium. (Li et al. *Nucleic Acids Res.* 21:1919-1925 (1993); Yang, et al., *Mol. Cell. Biol.* 21:7807-7816 (2001); Zhang, et al., *Proc. Nat'l. Acad. Sci. USA* 94:13437-13441

(1997); Robertson, et al., *J. Biol. Chem.* 243:82-91 (1968); J. J. Dunn, "The Enzymes", (P. D. Boyer, ed.), p. 485, Academic Press, New York (1982); D. Court, "Control of Messenger RNA lity" (J. G. Belasco and G. Brawerman, eds.), p. 71 Academic Press, New York (1993); and Nicholson, *FEMS Microbiol. Rev.*, 23:371 (1999)). Sun and Nicholson (*Biochem.*, 40:5102-5110 (2001)) utilized $Mn^{2+}$ ions to elucidate the reaction mechanism of the enzyme with a 60 base-long hairpin RNA corresponding to a known natural substrate of RNaseIII. This reference reported that in the presence of manganese, RNaseIII activity peaked at a 3 mM manganese ion concentration and then became rapidly diminished with increasing concentrations of manganese ions. Manganese was characterized as binding to an inhibitory site on the enzyme at high concentration.

Despite the unpromising outcome of substituting magnesium ions with other divalent cations in the prior art, the effect of manganese ions on RNaseIII was here investigated to determine the effect on cleavage of large double-stranded RNA. The findings reported herein provide the basis for new methods of generating low cost, biologically effective gene silencing reagents.

Advantages of the methods described herein include:

(a) obtaining an enhanced concentration of double-stranded RNA fragments of a size suitable for silencing of gene expression by a rapid, cost effective process that is not dependent on a gel based size separation step. The methodology provides hsiRNA mixtures which contain a plurality of double-stranded RNA fragments in which less than about 5% are uncut large double-stranded RNA and more about 8% have a fragment size of 18-25 base pairs. Indeed in embodiments of the method, mixtures may contain more than 15%, 20% or 40% fragments having a size of 18-25 base pairs. Because of its simplicity, this approach is amenable to automation and high throughput;

(b) forming a preparation of double-stranded RNA fragments with gene silencing activity without requiring identification of the particular fragment giving rise to the gene silencing effect;

(c) providing a means to utilize the products of the method by cloning individual fragments or forming libraries or arrays of clones to enable mapping these fragments with respect to the RNA from which they are derived as well as testing individual fragments for gene silencing activity;

(d) providing siRNA reagents for applications which include: silencing single genes or families of genes in a eukaryotic cell or organism to study function using standard transfection or transformation techniques for nucleic acids; and (e) using these siRNA reagents as therapeutic agents or in therapeutic agent screening or target validation assays.

The following terms as used in the description and in the accompanying claims have been defined below. These definitions should be applied unless the context in which the terms are used requires otherwise.

"hsiRNA mixture" refers to a heterogeneous (h) mixture of short double-stranded RNA fragments containing at least one fragment (siRNA) suitable for silencing gene expression. The RNA fragments in the hsiRNA mixture consistently contain a substantial fraction (greater than about 15% of the total number of fragments) having a length of 18-25 base pairs as determined by ethidium-stained native polyacrylamide gel analysis. The presence of fragments larger than 25 nucleotides or smaller than 18 nt is not excluded. The hsiRNA mixture is preferably obtained by digesting "large" double-strand RNA with RNAseIII in the presence of divalent transition metal cations, preferably manganese ions.

"Silencing" refers to partial or complete loss-of-function through targeted inhibition of gene expression in a cell and may also be referred to as "knock down". Depending on the circumstances and the biological problem to be addressed, it may be preferable to partially reduce gene expression. Alternatively, it might be desirable to reduce gene expression as much as possible. The extent of silencing may be determined by any method known in the art, some of which are summarized in International Publication No. WO 99/32619 incorporated herein by reference. Depending on the assay, quantitation of gene expression permits detection of various amounts of inhibition for example, greater than 10%, 33%, 50%, 90%, 95% or 99%.

"Large double-stranded RNA" refers to any double-stranded RNA having a size greater than about 40 base pairs (bp) for example, larger than 100 bp or more particularly larger than 300 bp. The sequence of a large dsRNA may represent a segment of a mRNA or the entire mRNA. The maximum size of the large dsRNA is not limited herein. The double-stranded RNA may include modified bases where the modification may be to the phosphate sugar backbone or to the nucleoside. Such modifications may include a nitrogen or sulfur heteroatom or any other modification known in the art. The double-stranded RNA may be made enzymatically, by recombinant techniques and/or by chemical synthesis or using commercial kits such as MEGASCRIPT® (Ambion, Austin, Tex.) and methods known in the art. An embodiment of the invention utilizes HiScribe™ (New England Biolabs, Inc., Beverly, Mass.) for making large double-stranded RNA. Other methods for making and storing large dsRNA are described in International Publication No. WO 99/32619.

The double-stranded structure may be formed by self-complementary RNA strand such as occurs for a hairpin or a micro RNA or by annealing of two distinct complementary RNA strands.

"Heterogeneous" in the context of an hsiRNA mixture refers to double-stranded RNA fragments having non-identical sequences produced from a single large double-stranded RNA or a mixture of large double-stranded RNAs after cleavage with RNaseIII in the presence of divalent transition metal ions. The fragments collectively contain sequences from the entire length of the large RNA and hence form a heterogeneous mixture.

"RNaseIII" refers to a naturally occurring enzyme or its recombinant form and may include mutants and derivatives or homologs. The utility of bacterial RNaseIII described herein to achieve silencing in mammalian cells supports the use of RNases from eukaryotes or prokaryotes in the present embodiments. Embodiments of the invention do not preclude the use of more than one RNase to prepare an hsiRNA mixture. RNaseIII as defined here is characterized by an amino acid consensus sequence in the protein [DEQ]-[kRQT]-[LM]-E-[FYW]-[LV]-G-D-[SARH] (PROSITE: PDOC00448 documentation for the RNaseIII).

Where units were used to describe concentrations of RNaseIII in present experiments, the formula for conversion to weight/volume is 32 units=1 μg/μl RNaseIII. Soluble bacterial RNaseIII enzyme can be readily purified from recombinant sources and is currently commercially available. (New England Biolabs, Inc., Beverly, Mass.).

"Complete digestion" refers to an RNaseIII reaction in which fragments of double-stranded RNA of a size greater than about 50 base pairs (excluding digested material retained in the loading well or bound to enzyme) are no longer readily detectable on an ethidium bromide stained 20% polyacrylamide gel.

"Host cell" refers to cultured eukaryotic cells or cells in animals, including vertebrates such as mammals including humans, and invertebrates such as insects. Host cell also refers to cells from plants and microorganisms.

"Overlapping" refers to when two RNA fragments have sequences which overlap by a plurality of nucleotides on one strand, for example, where the plurality of nucleotides (nt) numbers as few as 2-5 nucleotides or by 5-10 nucleotides or more.

"Complementary sequence" refers to a sequence which is not necessarily 100% identical to a sequence to which it hybridizes but nevertheless is capable of hybridizing to a specified nucleic acid under stringent conditions where stringent conditions may include: 400 mM NaCl, 40 mM PIPES pH 6.4, 1 mM EDTA, 50° C. or 70° C. for 12-16 hours followed by washing. Sequence variations can be tolerated such as those that arise due to genetic mutation, strain polymorphism, evolutionary divergence or chemical modifications.

"Part or all" of a messenger RNA refers to that part of the mRNA which is complementary to a large dsRNA.

"Substantial portion" refers to the amount of sequence of a large dsRNA represented in sequences contained in an hsiRNA mixture. In one embodiment, the representative sequence is greater than 20%. In other embodiments, the representative sequence may be greater than 30%, 40%, 50%, 60%, 70%, 80% or 90%.

"One or more dsRNAs" refers to dsRNAs that differ from each other on the basis of sequence.

"Target gene or mRNA" refers to any gene or mRNA of interest. Indeed any of the genes previously identified by genetics or by sequencing may represent a target. Target genes or mRNA may include developmental genes and regulatory genes as well as metabolic or structural genes or genes encoding enzymes. The target gene may be expressed in those cells in which a phenotype is being investigated or in an organism in a manner that directly or indirectly impacts a phenotypic characteristic. The target gene may be endogenous or exogenous. Such cells include any cell in the body of an adult or embryonic animal or plant including gamete or any isolated cell such as occurs in an immortal cell line or primary cell culture.

The introduction of an hsiRNA mixture into vertebrate, invertebrate, plant or protoplast cells, or micro-organisms may be achieved directly into the cell or introduced extracellularly into a cavity or interstitial space, into the circulation of an organism, orally, by bathing, transdermally, by a transmucosal route, topically or by use of viral vectors to infect the host with the DNA.

Standard protocols of transfection or transformation may be used for introducing siRNA into cells in culture, for example, protocols using Lipofectamine 2000, oligofectamine (Invitrogen, Carlsbad, Calif.), TRANS-IT TKO® (Mirus Corp., Madison, Wis.), Targefect (Targeting Systems, Santee, Calif.), calcium phosphate or electroporation. Engineered vectors containing fragments from hsiRNA or siRNA can include bacterial vectors, plasmids or viral vectors for transforming or transfecting whole organisms. A gene gun may be utilized for plants for directing dsRNA into chloroplasts for example. The methodology for introducing foreign nucleic acids into organisms and cells is well known in the art. Introduction of the hsiRNA mixture of DNA clones expressing individual fragments from a particular hsiRNA mixture into whole animals can be achieved by means of standard techniques for introducing nucleic acids.

In this specification and the appended claims, the singular forms of "a", "an" and "the" include plural reference unless the context clearly dictates otherwise.

Conditions for Cleavage

While particular conditions of cleavage are provided here below, these conditions are not intended to be limiting. Equivalent formulations and buffers may be readily substituted for the present embodiments.

An hsiRNA mixture may be formed from a large double-stranded RNA, an RNaseIII enzyme and a standard buffer containing a divalent transition metal. The preferred transition metal is manganese but cobalt, nickel, cadmium, zinc or other metal transition ions may also be used to generate hsiRNA (Example II). Formation of the desired reaction product is not very sensitive to metal ion concentration (Example I). FIG. 1A showed that concentrations of $MnCl_2$ of about 5-50 mM manganese ion concentration produced the desired hsiRNA mixture. A preferred concentration appears to be in the range of about 10 to 20 mM manganese ions.

Various enzyme reaction parameters were optimized for digestion of large double-stranded RNA substrate to form an hsiRNA mixture as follows:

(a) Buffer conditions: Buffer solutions made from 50 mM NaCl, 10 mM Tris-HCl at pH 7.9 (25° C.), 1 mM DTT and further including the selected transition metal or 100 mM NaCl, 50 mM Tris-HCl, 1 mM DTT and 10 mM $MnCl_2$ at pH 7.5 (25° C.) were used in the Examples. However, it is within the scope of the present embodiment to utilize an alternative buffer and salt at various concentrations. Similarly, it is within the scope of the embodiment to vary the pH. A preferred pH range is about pH 7 and 8.5.

(b) Time of the reaction: The cleavage reaction yielding a hsiRNA mixture with RNaseIII in the presence of a transition metal ion in particular, manganese ions, was achieved within 10 mins (FIG. 1E). A similar amount of an hsiRNA mixture was shown to be achieved by extending the incubation to 180 minutes (FIG. 1E). It is envisaged that the reaction time is not a highly critical parameter and depending on convenience of the experimenter, a reaction time of less than 10 mins or greater than 180 minutes may be utilized for example, 4 hours or 6 hours or longer. Reaction times of less than 1 minute or as short as 5 seconds have been used with successful results.

(c) Concentration of enzyme in the reaction mixture: When the enzyme was titrated and the reaction product analyzed on gels, FIG. 1B showed that a final concentration of greater than 0.025 µg/µl RNaseIII was sufficient to completely digest 2.5 µg double-stranded RNA of a size of 1000 bases (total volume 50 µl). In Example I, the maximum yield of hsiRNA was calculated to result from digesting 0.056 µg/µl of 1000 bp dsRNA with 0.1 µg/µl of RNAseIII for 30 mins at 37° C. (which corresponded to about 1 RNaseIII monomer for every 22 bp double-strand RNA equivalent).

(d) Amount of RNAseIII enzyme to substrate (w/w):

Ratios of RNaseIII enzyme to substrate (w/w) can be used in a range of about 0.005:1 to 25:1 in the presence of a divalent transition metal ion to cleave large double-stranded RNA into an hsiRNA mixture. Indeed, high concentrations of RNaseIII relative to substrate such as a ratio of about 2:1 to 3:1 w/w may be effectively used in the absence of transition metal divalent cations to yield a band corresponding to 21-23 nt on a polyacrylamide gel. The amount of material in the band increases with the increased ratio of enzyme to substrate. However, the yield obtained in the absence of transition metal divalent cations is substantially less than in the presence of transition metal divalent cations.

FIG. 1B describes the products of cleavage using a ratio within the range of about 0.0125:1 to 8.8:1 enzyme to substrate, with a preferred ratio being greater than or equal to about 0.25:1. FIG. 1B shows that a ratio of 0.5:1 w/w of enzyme to substrate in FIG. 1B completely digested large double-stranded RNA in the presence of manganese ions. Cleavage at high concentration ratios of RNaseIII to large dsRNA (for example, 0.25:1 to 2:1 to 15:1 mass per mass) yields improved yields of the fractions corresponding to 15-30 nucleotides, in particular 21-23 nucleotides. High concentrations of enzyme in the presence of manganese ions further enhance the yield of fragments of the desired size.

(e) Use of transition metal divalent cations in addition to manganese:

An hsiRNA mixture can be generated in the presence of divalent transition metal ions $Co^{2+}$, $Ni^{2+}$, $Cd^{2+}$, or $Fe^{2+}$ in addition to manganese ions (for example as shown in FIG. 2 and Example II). For example, $MnCl_2$, $CoCl_2$, $NiSO_4$, $CdCl_2$, or $FeSO_4$ may be added to the reaction mixture in a concentration range of 0.1-100 mM, more preferably, 5-100 mM, for example, 10-20 mM. Whereas the parameters of optimizing the reaction have been described in most detail herein for manganese, it is envisaged that optimum reaction conditions for RNaseIII in the presence of other divalent transaction metals will be determined for pH, buffer conditions, temperature, time of reaction, concentration and ratio of enzyme to substrate determined using the approach described in Examples I-VII. A superior performance of RNaseIII in the presence of a 10 mM concentration of various divalent transition metal cations compared with that of magnesium for generating hsiRNA mixtures has been established (FIG. 1A and FIG. 2).

One of the problems in the field of gene silencing is that of identifying a short double-stranded RNA (15-30 bp) that can achieve the desired goal of effectively targeting a particular messenger RNA for cleavage. In embodiments of the invention, this problem is solved by utilizing a large double-stranded RNA having a sequence that is identical to all or part of the target mRNA including untranslated mRNA and cleaving this large RNA into multiple overlapping fragments of the appropriate size for gene silencing. Examples III and IV demonstrate that the cleavage products are representative of the entire length of the large double-stranded RNA and Example VI shows that the hsiRNA mixture contains within it fragments that are capable of gene silencing by transfecting a variety of cells including insect cells and mammalian cells.

Once an hsiRNA mixture is obtained, it is possible to make a library of clones containing DNA sequences corresponding to individual double-stranded RNA fragments in the mixture (Example IV). When provided with appropriate promoters, individual clones can be used to transfect cells so as to provide a continuous supply of the short doubled-stranded RNA for use in long-term gene silencing. Silencing of gene expression as a result of transfection of an individual clone or selected mixtures of clones into a target cell or organism may have particular advantages in for example, therapeutic applications, over transient gene silencing effects achieved by transfecting cells with the double-stranded RNA itself. This provides new reagents for therapeutic applications providing an unlimited supply of an agent that specifically modulates gene expression of a particular gene.

Other advantages of obtaining clones of individual fragments, as described herein, include (a) a resource for understanding which single fragment or subset of fragments in a mixture of fragments formed by cleavage of double-stranded RNA is capable of gene silencing while other fragments in the mixture are not; (b) a means of studying why some RNA fragments are efficacious in gene silencing and others are not; (c) establishing the specificity of a particular hsiRNA for a particular mRNA; (d) establishing the unique characteristics of an hsiRNA mixture from a particular RNaseIII versus a different RNaseIII, and (e) characterizing the site at which hsiRNA induces cleavage on a target mRNA; and (f) the generation of computer algorithms for the design of synthetic siRNA based on statistical analysis of the cloned fragments.

Specificity of Gene Silencing

Specificity of gene silencing for a particular targeted mRNA can be confirmed using a BLAST analysis of sequences in the targeted mRNA to determine that no extended regions in the RNA (over 20 bases long) are identical to other gene transcripts to avoid non-specific gene silencing.

Using the methods described herein, hsiRNA preparations that are specific for a single member of a gene family and do not silence mRNA from other members of that gene family can be prepared from long dsRNA that is complementary in sequence to a segment of the target mRNA (also referred to as long dsRNA segments). Alternatively, hsiRNA preparations can be prepared that have specificity for any gene in a gene family but do not have specificity for other genes outside the gene family.

The appropriate gene silencing effect may be achieved by targeting mRNA sequences that are unique or that form part or all of a consensus region for a family of mRNAs.

A "super potent" mixture of siRNA fragments may be prepared according to the present methods in which individual siRNA fragments that have been optionally cloned and have been identified as triggering cleavage at a site on the target mRNA are combined to obtain a mixture with the desired gene silencing effect.

One of the advantages of present embodiments is the ability to rapidly prepare a mixture of hsiRNA fragments that can be tested in vivo for activity and from which subsets of fragments having particular sequence specificities can be selected as desired without the need for expensive chemical synthesis of oligonucleotide fragments or the more haphazard approach offered by partial enzymatic digestion or by crude extracts of cells containing naturally occurring DICER. A benefit of the RNaseIII digest in the present of divalent cations is that the entire large dsRNA is substantially represented by overlapping fragments. FIG. 4 shows that more than 50% of the sequence of NheI-BsrGI GFP fragment is covered by complementary siRNA fragments of the hsiRNA mixture. It is anticipated that this % representation is an under-estimate. There is an apparent bias of clones obtained from one strand in comparison to the other strand which may be related to the specific primers used as linkers or to partial sampling of cloned fragments.

Insights into gene silencing can be achieved by varying the size and sequence characteristics of the large RNA with respect to the target mRNA that is expressed from the template DNA. For example, serially deleted or randomly cut DNA templates can be used for the generation of variable size dsRNAs, which upon digestion with RNaseIII as described herein, can be tested for effectiveness in silencing (Example VIII).

Example VIII shows how dsRNA corresponding to segments of a mRNA and subjected to RNaseIII digestion in the presence of a divalent cation, are effective in knock-down gene expression in cell cultures. Different segments may produce mixtures that vary in the extent of knock-down activity. For example, this approach may be used to understand the regulatory functions of long terminal repeat (LTR) regions adjacent to translated sequences in mRNA.

The knock-down of DnMT1 by hsiRNA corresponding to DnMT1 segments 1, 3 or 2 (in order of increasing effectiveness) was detected by the decrease or absence of the corresponding protein band (compare lanes 4, 5 and 6 with lanes 2 and 3 (top panel). In all three cases tested, (segments 1, 2 and 3) the hsiRNA-treated cells showed effective knock-down of the expression of the target DnMT1. The silencing efficiency of segment 2 hsiRNA was higher than that of segments 1 and 3 hsiRNAs. Conversely the p53 band intensity was unaffected by all hsiRNA mixtures corresponding to DnMT1 (FIG. 10C).

The simplicity of testing hsiRNA from different segments provides a rapid primary screening of a target sequence for determining the activity of siRNA molecules in a heterogeneous siRNA mixture.

The methods described herein can also be applied to producing multiple hsiRNA mixtures which can then be used to simultaneously silence multiple genes. Additional uses include targeting upstream or downstream regulatory regions with hsiRNA to modulate expression. Accordingly, a mixture of large dsRNA obtained by transcription of a collection of DNA templates can be digested by RNAseIII in the presence of divalent transition metal ions and/or high concentrations of the enzyme in a single reaction (multiplexing). A methodology for making large double-stranded RNA is provided in Example VII.

The above described generation of hsiRNA mixtures or clones thereof for making selected siRNA fragments can be achieved in part or as a whole by utilizing a kit of the type described in Example VII. Instructions are provided for making a desired large double-stranded RNA, for generating hsiRNA mixtures and for transfecting cells with such mixtures. mixtures may then be cloned and their sequences analyzed and mapped.

Site Specific Cleavage of Target mRNA

As described herein, the set of dsRNA fragments produced by cleavage of large dsRNA with RNaseIII under conditions of high concentration or/and in the presence of transition metal cations is a heterogenous mixture of overlapping fragments. This mixture is capable of silencing a gene presumably by cleaving a mRNA transcript of a target gene where the large dsRNA is complementary to sequences in the mRNA. Analysis of the hsiRNA mixtures produced, using for example the methodology of Example IV and VI, permits the characteristics of the most effective target sequences to be defined with single nucleotide resolution.

Mechanistic studies on RNAi have demonstrated that active siRNAs result in site-specific cleavage of the target mRNA by guiding to the target sequence the RISC complex containing a specific nuclease (Hannon et al. *Nature* 418:244-251 (2002), Zamore et al. *Cell* 101:25-33 (2000) and Elabshir et al. *Genes Dev.* 15:188-200 (2001)). Fragments of mRNA cleaved by the RISC complex are detectable in Northern Blots (Amarzguioui, et al., *Nucleic Acids Res.* 31:589-595 (2003)). The nucleotide position of each cleavage event is found 10 base residues from the end of the mRNA corresponding to a sequence location that is central in a 21 nucleotide siRNA (Martinez et al. *Cell* 110:563-574 (2002)). The RISC cleavage site on the mRNA can thus be used to infer the sequence of the corresponding siRNA which guided this cleavage event.

Starting with an hsiRNA mixture which has gene silencing activity such as described in Examples VI and VIII, it is possible to analyze one or more cleavage sites on the target mRNA using standard methodologies such as RNase protection analysis and Primer extension analysis (Sambrook and Russell. Molecular Cloning: A Laboratory Manual, (3rd ed.) Cold Spring Harbor Press (2001)). For example, a hypothetical cleavage site at nucleotide X in target mRNA (i) may infer an siRNA (ii). Individual inferred siRNA sequences may then be synthesized and tested for validation:

(i) target mRNA

NNNNNNNN$_{-10}$NNNNNNNNNXNNNNNNNNNN$_{+10}$NNNN (ii) siRNA

N$_{-10}$NNNNNNNNNXNNNNNNNNN N$_{+10}$

The above approach has been exemplified in Example IX and FIG. 11.

Another advantage of present embodiments is that once a single siRNA fragment or specific mixture or subset of hsiRNA fragments are obtained, they can be cloned as described in Example IV and V to provide a continuous or in vivo regulated Example IV and V to provide a continuous or in vivo regulated supply of these nucleic acids without the need for de novo synthesis for each experiment.

Illustrative Uses

The availability of cloned fragments provides not only a continuous supply of a reagent or therapeutic agent but also a novel therapeutic approach in which a desired knockdown effect can be maintained by gene therapy techniques in a whole organism without repeated administration of the siRNA fragment. Clones expressing siRNA fragments or hsiRNA mixtures can be used for complete, modulated or transient in vivo silencing of a target gene.

A gene derived from any pathogen can be targeted for inhibition. For example, the gene could cause immunosuppression of the host directly or be essential for replication of the pathogen, transmission of the pathogen or maintenance of the infection. The inhibitory RNA could be introduced in cells in vitro or ex vivo and then subsequently placed into an organism to effect therapy, or the organism could be directly treated by in vivo administration. A method of gene therapy can be envisioned. For example, cells at risk for infection by a pathogen or already infected cells, particularly human immunodeficiency virus (HIV) infections, may be targeted for treatment by introduction of RNA according to the invention. The target gene might be a pathogen or host gene responsible for entry of a pathogen into its host, drug metabolism by the pathogen or host, replication or integration of the pathogen's genome, establishment or spread of an infection in the host, or assembly of the next generation of pathogen. Methods of prophylaxis (i.e., prevention or decreased risk of infection), as well as reduction in the frequency or severity of symptoms associated with infection, can be envisioned.

The present invention could be used for treatment or development of treatments for cancers of any type, including solid tumors and leukemias, examples of which are listed in International Publication No. WO 99/32619.

The present invention is further illustrated by the following Examples. These Examples are provided to aid in the understanding of the invention and are not construed as a limitation thereof.

The references cited above and below are herein incorporated by reference.

Example I

Preparation of an hsiRNA Mixture

Determining the Effect of Manganese Ions on Cleavage of dsRNA by RNaseIII.

Full length double-stranded RNA (dsRNA) corresponding to the gene of interest, in this Example hu PKR, was generated using the HiScribe™ RNAi Transcription Kit (New England Biolabs, Inc., Beverly, Mass.). Methods for creating double-stranded RNA are described in detail in Example VII.

A 0.4 kb double-stranded RNA molecule (0.25 µg) was digested with 30 units E. coli RNaseIII (0.9 µg) (New England Biolabs, Inc., Beverly, Mass.) in 20 µl of buffer consisting of 100 mM NaCl, 50 mM Tris-HCl, 5, 10, 20 or 50 mM $MnCl_2$ or 10 mM $MgCl_2$ (control), 1 mM dithiothreitol (pH 7.5 @ 25° C.) at 37° C. Samples containing 50-100 mM $MnCl_2$ are also tested to provide complete digestion of the long double-stranded RNA.

Digestion products of RNaseIII in the presence of various concentrations of manganese ion were enriched in the size range of 18-25 bp. The mixture of fragments obtained thus are here designated as an hsiRNA mixture. In contrast, digestion of double-stranded RNA with the RNaseIII in 10 mM $Mg^{2+}$ buffer absent manganese ions produced a heterogeneous size mixture of fragments resulting from partial digestion in which the predominant size was smaller than the desired 20-40 bp fragments that characterize hsiRNA (FIGS. 1A and 2). The digestion product of RNAseIII in the presence of magnesium ions was found to be substantially ineffective in gene silencing (FIGS. 1A, 2 and 5).

Production of hsiRNA from a 1 kb dsRNA Using Varying Amounts of RNaseIII.

A 1 kb (SphI-NgoMIV) fragment from GL3 luciferase was cloned in Litmus 38i. Double-stranded RNA was generated using the HiScribe™ kit (New England Biolabs, Inc., Beverly, Mass.) from a DNA template generated as described in Example VII (using biotinylated T7 primer PCR). 2.5 µg of dsRNA was digested with 0.5, 1, 2, 4, 8, 16 µL of a 1.36 mg/mL RNaseIII stock solution in a 50 µL reaction mix (corresponding to a final concentration in the reaction mix of 0.012, 0.025, 0.050, 0.11, 0.22 and 0.44 µg/µl) The reaction was carried out for 20 minutes in the buffer 50 mM NaCl, 50 mM Tris-HCl, 20 mM $MnCl_2$, 1 mM dithiothreitol (pH 7.5 @ 25° C.), and was stopped with the addition of EDTA to provide a final concentration of EDTA of 25 mM. 40 µL from each reaction was analyzed by 20% native PAGE (FIG. 1B). The major digestion product detected co-migrates with a single sequence synthetic siRNA (FIG. 1B, compare lanes 5, 6, 7 and 8 with lane 1). The digestion was judged complete when at least 2 µL of RNaseIII (FIG. 1B, lane 5 using 0.05 µg/µl final concentration of RNaseIII) was utilized. Fluorescence gel densitometry was used to measure the relative amount of hsiRNA produced as a function of RNaseIII concentration. The maximum yield of hsiRNA is obtained with 4 µL of RNaseIII (0.11 µg/µl final concentration) in this experiment.

Relevant and Generalization of the Optimal Ratio of RNaseIII to Substrate

To further define the optimal concentrations of RNaseIII for the production of hsiRNA, the hsiRNA yield was monitored in digestion of a second substrate using varying concentrations of RNaseIII. RNaseIII concentrations ranging from 0.025 to 3.2 units/µl were used (where 32 units correspond to 1 µg of RNaseIII providing 0.0007 to 0.1 µg/µl final concentration) to digest 0.056 µg/µl of dsRNA substrate (~1000 bp, part of C. elegans chitin synthase gene) in 10 µl reactions containing 50 mM Tris-HCl, pH 7.5, 100 mM NaCl, 1 mM DTT, 10 mM $MnCl_2$. The reaction mixture was incubated at 37° C. for 30 min. RNaseIII digestion was stopped by adding 0.5 µl of 0.5M EDTA. A fraction of each reaction (2.5 µl, equivalent to 0.14 µg dsRNA substrate) together with 1 µl of loading buffer (containing xylene cyanol and bromophenol blue) was analyzed by native 20% PAGE (FIG. 1C).

In a separate experiment dsRNA at concentrations of 0.06, 0.12, 0.24 and 0.47 µg/µl were digested with 3.2 units/µl of RNaseIII (0.1 µg/µl) under the same reaction conditions described above (FIG. 1D).

In this Example, the maximum yield of the hsiRNA was obtained with 0.1 µg/µl of RNaseIII for 0.056 µg/µl dsRNA substrate, or 57 units RNaseIII per µg dsRNA (FIG. 1C Lane 2). At this concentration ratio, there is about one RNaseIII monomer molecule for every 22-bp long dsRNA segment. Half this ratio of enzyme to substrate (FIG. 1C, lane 3) yielded slightly less hsiRNA. Similarly, in FIG. 1D, lanes 3 or 4, a maximal amount of an hsiRNA was obtained. With decreasing amount of RNaseIII, there is less hsiRNA accumulation and the dsRNA was cleaved to larger fragments.

These experiments suggest that 25-50 units of RNaseIII per µg of dsRNA in a 10 µL reaction produce an optimal yield of hsiRNA.

A Time Course Study of Double-Stranded RNA Cleavage

The kinetics of hsiRNA production was monitored by a time-course study. A digestion reaction was performed for varying lengths of time using an optimal RNaseIII:dsRNA ratio (dsRNA at 0.056 µg/µl, RNaseIII at 3.2 units/µl (0.1 µg/µl) in the presence of a buffer containing 10 mM $Mn^{++}$. After adding all components, the reaction was vortexed briefly to mix and incubated at 37° C. At various times during the incubation, 10 µl of the reaction was removed and stopped with 0.5 µl of 0.5 M EDTA. Samples were kept on ice before analysis on 20% native PAGE gel (FIG. 1E).

From this experiment, it is apparent that the RNaseIII digestion in the presence of $Mn^{++}$ is rapid in producing the hsiRNA band. After 10 minutes of incubation, the production of hsiRNA is quantitative and no dsRNA larger than the hsiRNA is detectable.

Preparation of Purified hsiRNA

Large amounts of purified hsiRNA were obtained by High Performance anion exchange column chromatography of RNaseIII digested dsRNA through a Q Sepharose column (Pharmacia, Piscataway, N.J.) in 10 mM Tris-HCL, ph 7.5. (FIG. 1F). Purified hsiRNA of ~18-25 bases eluted from the column at 0.40-0.45 M NaCl, away from RNaseIII (elutes at 0.025-0.2 M NaCl) and dsRNA of 30-1000 bases (elutes at 0.5 M and higher NaCl). Lane 5 and 6 show a major band containing large amounts of hsiRNA and insignificant amounts of RNA of other sizes.

Based on load and gradient profile adjustment, concentrations of hsiRNA of range 1 µg to 1 mg/ml or higher can be obtained without contaminating protein or high molecular weight dsRNA or DNA. Such high concentrations of purified hsiRNA may be used as an in vivo reagent or therapeutic where separation of any contaminating artifacts is necessary for FDA approval.

Example II

Preparation of hsiRNA Using Various Divalent Metal Ions

To determine the effect of various divalent cations on the cleavage products of RNaseIII, the following experiment was undertaken: 1 μg of a large double-stranded RNA molecule (800 bp) was digested with each of two concentrations of *E. coli* RNaseIII (0.04 μg/μl or 0.02 μg/μl) at pH 7.5 (25° C.) in 50 μL of buffer containing 100 mM NaCl, 50 mM Tris-HCl, 1 mM dithiothreitol and either 10 mM $MgCl_2$ at 37° C. (lanes 1 and 2), 10 mM $MnCl_2$ (lanes 3 and 4) 10 mM $CoCl_2$ (lanes 5 and 6) or 10 mM $NiSO_4$ (lanes 7 and 8) for 30 minutes. The results are shown in FIG. 2. A double-stranded RNA product having an approximate size of 22 bp (within a range of 20 bp-40 bp) was produced by complete digestion of the large double-stranded RNA in the presence of 0.04 μg/μl RNaseIII and 10 mM manganese ions. Digestion with 0.04 μg/μl RNaseIII in the presence of 10 mM $Mg^{2+}$ buffer absent manganese ions produced fragments which were smaller than the desired 18-25 bp long (lanes 1 and 2) and were found not to be suitable for RNAi-silencing experiments. In contrast, the fragments produced in the presence of cobalt or nickel in addition to manganese provided a larger fraction of the desired fragments of 18-25 bp in length than was obtained in the presence of magnesium ions.

Example III

Short Double-Stranded RNA Cleavage Products of RNaseIII Digestion Contain Sequences Representing the Entire Parent Sequence The DNA template for transcription of p53 (1.1 kb fragment encoding amino acids 100-393) was digested with the restriction enzyme AciI and the resulting fragments separated on an agarose gel. The gel was ethidium-stained, photographed and subsequently transferred to a nylon membrane (Hybond® N+, Amersham, Piscataway N.J.).

Double-stranded RNA synthesized by in vitro transcription of the 1.1 kb fragment was digested with RNaseIII at a final concentration of 0.04 μg/μl in the presence of 10 mM $Mn^{++}$ at pH 7.5 and 25° C. for 30 minutes as described in Example II and the products were separated on a 20% native polyacrylamide gel.

The products of the digestion (the hsiRNA mixture) were visualized by ethidium bromide staining and the fraction corresponding to about 21 bp was excised in a small gel slice and purified by electro-elution for 20 min in a small tube sealed with dialysis membrane, and ethanol precipitated as described in Example IV below. The purified short RNA labeled with cytidine 3', 5' bis(phosphate) [5'-$^{32}$P] and T4 RNA ligase as recommended by the manufacturer (New England Biolabs, Inc., Beverly Mass.). The $^{32}$P-labeled RNA was used to probe the Southern blot of same gel at 48° C. overnight in 0.5 M sodium phosphate pH 7.5, 7% SDS, 1% BSA. The blot was washed at the same temperature three times for 30 min in 50 mM sodium phosphate pH 7.5, 0.1% SDS, and subsequently exposed to x-ray film.

The autoradiogram shows that all the fragments of the DNA template collectively used to produce the hsiRNA mixture were hybridized by the probe, whereas unrelated DNA fragments present in large amounts in the size marker did not (FIG. 3A compare lanes 2 and 3).

The film was scanned to quantify the relative amount of probe. The radioactive intensity was plotted against the size of the bands. FIG. 3B shows that the amount of probe for each band is proportional to the size of the fragment, and similar to the amount of ethidium bromide fluorescence corresponding to each fragment. These results indicate that the short RNA fragments of size 15-30 bp produced by RNaseIII digestion in the presence of $Mn^{++}$ contain fragments from the entirety of the parent sequence.

Example IV

Cloning and Sequencing hsiRNA Fragments

Products from RNaseIII digestion were cloned using a strategy in which primer annealing sites were successively ligated to each end of a strand of digested RNA (FIG. 4A). The order of ligation was precisely controlled by differential phosphorylation of the species being ligated, which also prevented polymerization of any of the species during any of the ligation steps. The resulting RNA-DNA chimerae were then amplified by RT-PCR and cloned into a plasmid vector for sequencing. Alternatively, second strand cDNA synthesis with a single primer can be carried out as an alternative to the PCR step.

The ligated oligonucleotides consisted of defined sequences (not polyadenylated) and were composed of DNA exclusively unlike those in Elbashir, et al., *Genes and Development* 15:188-200 (2001); Lau, et al., *Science,* 294:858-862 (2001) and Lee, et al., *Science,* 294:862-864 (2001). Also, to prevent self-polymerization in the ligation reaction, Primer 1 was synthesized with a 5' and 3' phosphate group. To construct the final library from the cDNA generated by RT PCR, DNA fragments were amplified and directly cloned into plasmid pUC19 (not concatamerized before cloning).

1. Generation of dsRNA:

Full length double-stranded RNA (dsRNA) corresponding to Maltose Binding Protein (malE) was generated using the HiScribe™ RNAi Transcription Kit (New England Biolabs, Inc., Beverly, Mass.). To generate templates for in vitro transcription, the pLITMUS28i plasmid containing the 808-bp BglII-EcoRI fragment of malE was used in a PCR reaction to amplify the gene fragment. The PCR was performed using Vent® DNA polymerase (New England Biolabs, Inc., Beverly, Mass.) in 1× ThermoPol Reaction Buffer [20 mM Tris-HCl, pH 8.8, 10 mM KCl, 10 mM $(NH_4)_2SO_4$, 2 mM $MgSO_4$, 0.1% Triton X-100] supplemented with 0.4 μM T7 minimal primer d(5'-TAAACG ACTCACTATAGG-3' (SEQ ID NO:3)), 400 μM dNTPs and approximately 20 ng of plasmid DNA in a 50 ul volume. The PCR protocol used 25 cycles, each consisting of 94° C. for 30 seconds, 50° C. for 30 seconds, 72° C. for 30 seconds. Both digests and PCR reactions were phenol/chloroform extracted and ethanol precipitated using standard molecular biology techniques and then resuspended in TE buffer (10 mM Tris-HCl, pH 8.0, 1 mM EDTA) to a final concentration of 1 mg/mL each (restriction digests) or 125 μg/mL (PCR product). These templates were then used in large scale in vitro transcription reactions to generate large dsRNA.

Large scale in vitro transcription reactions were scaled up to a total volume of 300 μL or 10× the pilot reaction described by the manufacturer. A double-strand DNA template was similarly prepared from Litmus 38i containing the 731-bp NheI-BsrGI fragment of GFP. For the GFP dsRNA, 10 μL of each digested template were used and for the malE gene fragment, 40 µL of PCR reaction was used per reaction. Reactions contained 40 mM Tris-HCl, pH 8.1, 19 mM MgCl$_2$, 5 mM DTT, 1 mM spermidine, 4 mM each rNTP, 50 µg/mL BSA, 3 units/µL yeast inorganic pyrophosphatase, 400 units/mL placental RNase inhibitor, and 5000 units/mL T7 RNA polymerase. The reactions were incubated at 42° C. for 2 hours, 65° C. for 10 minutes and then stored at −20° C. In preparation for RNaseIII digestion, the dsRNA was purified by electrophoresis on an 8% polyacrylamide gel and excising bands corresponding to the correct size were excised (829 bp and 908 bp respectively for GFP or malE). The dsRNA was eluted from the gel slice by incubating at 37° C. with shaking in 400 µL RNA elution buffer (0.1 M sodium acetate, pH 4.8, 1 mM EDTA, 0.1% SDS) overnight and an additional 400 µL for 4 hours. Eluate samples were pooled, phenol/chloroform extracted to remove gel residue and SDS, ethanol precipitated and resuspended in 100 µL Tris EDTA (TE) buffer.

2. RNaseIII Digestion of Full Length malE dsRNA:

An RNaseIII digestion was carried out to generate small RNA duplexes of 22 bp in length from the malE sequence. Reactions containing 4 µg of full-length malE dsRNA in 0.1 M NaCl, 50 mM Tris-HCl, pH 7.9, 10 mM MnCl$_2$, 1 mM dithiothreitol and 4 µg of RNaseIII (New England Biolabs, Inc., Beverly, Mass.) in a total of 160 µL were incubated at 37° C. for 30 minutes. Samples were then phenol/chloroform extracted and ethanol precipitated to remove RNaseIII and recover the RNA fragments. Small RNA fragments were then treated with Calf Intestinal Alkaline Phosphatase (CIP) (Roche Diagnostics, Mannheim, Germany) to prevent polymerization during the subsequent ligation reaction. This was accomplished by preheating the sample to 50° C. for 5 minutes and treated with CIP in a standard reaction as described by the manufacturer using 2.5 units of CIP per µg of RNA in 50 mM Tris-HCl, pH 8.5, 0.1 mM EDTA. Reactions were carried out at 50° C. for 1 hour followed by phenol/chloroform extraction and ethanol precipitation. Desphosphorylated RNA fragments were then resuspended in 25 µL of TE.

3. Ligation of Small RNA Fragments to Primer 1:

Small RNA fragments (entire 4 µg sample from above) were then ligated at their 3' end to Primer 1, d(5'p-CTGCAGG ATATCT<u>GGATCC</u>AC-p-3' (SEQ ID NO:4)), containing a BamHI restriction site (underlined). RNA fragment duplexes were first denatured by heating to 70° C. for 5 minutes and then placing on ice. The ligation was carried out in 60 µL containing 50 mM Tris-HCl, pH 7.8, 10 mM MgCl$_2$, 10 mM dithiothreitol, 1 mM ATP supplemented with 10% (v/v) DMSO, 10 µg of Primer 1 and 120 units of T4 RNA ligase (New England Biolabs, Inc., Beverly, Mass.) at 20° C. for 24 hours. The ligation products were then gel purified by electrophoresing on a denaturing 12% polyacrylamide gel containing 7 M urea and excising bands approximately 45 nt in length. Ligation products were eluted from the gel using RNA elution buffer, recovered by ethanol precipitation as described above and resuspended in 10 µL of TE.

4. Ligation of Intermediate to Primer 2:

The 5' RNA end of the ligation product above was phosphorylated using 3'-phosphatase free T4 polynucleotide kinase (T4 PNK, (Roche Diagnostics, Mannheim, Germany)) to avoid polymerization in the subsequent ligation reaction. The phosphorylation was carried out with the entire sample from above at 37° C. for 30 minutes in 20 µL containing 50 mM Tris-HCl, pH 7.8, 10 mM MgCl$_2$, 10 mM dithiothreitol, 1 mM ATP (1×T4 RNA ligase buffer from New England Biolabs, Inc. (Beverly, Mass.) and 10 units of T4 PNK. T4 PNK was then heat inactivated by incubating at 65° C. for 20 minutes.

Phosphorylated small RNA fragments ligated to Primer 1 were then ligated at their 5' end to Primer 2 d(5'-CATGCCCG <u>G</u> <u>GTACC</u>TTTCTATTCTC-3' (SEQ ID NO:5)) containing an Acc65I restriction site (underlined). The ligation was carried out in 30 µL containing 1×T4 RNA ligase buffer supplemented with 10% DMSO, 1 µg of Primer 2 and 60 units of T4 RNA ligase at 20° C. for 24 hours. The ligation product was then gel purified by electrophoresing on a denaturing 12% polyacrylamide gel containing 7 M urea and excising bands at approximately 70 nt. Ligation products were eluted from the gel using RNA elution buffer, recovered by ethanol precipitation as described above and resuspended in 10 µL of TE.

5. Reverse Transcription and PCR Amplification of RNA/Primer Hybrid for Cloning:

The product of small RNAs ligated at the 5' and 3' ends with Primers 2 and 1 respectively was then reverse transcribed to make a double-stranded duplex for subsequent PCR amplification. Reverse transcription was carried out using Primer 3 d(5'-GT<u>GGATCC</u>AGATATCCTGCAG-3' (SEQ ID NO:6)), also known as the Litmus 28/38 reverse sequencing primer (New England Biolabs, Inc., Beverly, Mass.), with a BamHI site (underlined). The entire sample from above was mixed with 0.1 µM Primer 3 and 0.5 mM dNTPs, then heated to 65° C. for 5 minutes with subsequent cooling on ice to anneal Primer 3 to the 3' end of the ligation product (Primer 3 is complementary to Primer 1). A reaction volume of 19 µL containing 50 mM Tris-HCl, pH 8.3, 75 mM KCl, 3 mM MgCl$_2$ and 10 mM ditiothreitol was incubated at 42° C. for 2 minutes before adding 200 units of M-MuLV reverse transcriptase (New England Biolabs, Inc., Beverly, Mass.) and then at 25° C. for 10 minutes, 42° C. for 50 minutes and 70° C. for 15 minutes. Duplex DNA was then obtained by PCR amplification of the cDNA product of the reverse transcription. The PCR was performed using Deep Vent® DNA polymerase (New England Biolabs, Inc., Beverly, Mass.) in 1× ThermoPol Reaction buffer supplemented with 0.2 µM each of Primers 2 and 3, 400 mM dNTPs and 2 µL of the reverse transcription reaction in a final volume of 100 µL. The PCR protocol used 25 cycles, each consisting of 94° C. for 30 seconds, 60° C. for 30 seconds, 72° C. for 30 seconds. The ~70-bp PCR product was gel purified by excising from an 8% nondenaturing polyacrylamide gel as described above, recovered by ethanol precipitation and resuspended in 50 µL TE.

6. Cloning of PCR Fragments into pUC19:

PCR fragments were cloned into the pUC19 plasmid (New England Biolabs, Inc., Beverly, Mass.) via BamHI and Acc65I restriction sites by standard molecular cloning techniques. Briefly, the pUC19 digest was performed in 1×NEBuffer 3 (0.1 M NaCl, 50 mM Tris-HCl, pH 7.9, 10 mM MgCl$_2$, 1 mM dithiothreitol) supplemented with 0.1 mg/mL BSA, 8 units of BamHI and 4 units of Acc65I per µg pUC19. Digestion was carried out at 37° C. for 3 hours. Digested pUC19 plasmid was gel purified by electrophoresing on a 1% low melt agarose gel and recovering DNA from the excised gel slice using β-agarase (New England Biolabs, Inc., Beverly, Mass.) according to the manufacturer's instructions. PCR fragments were digested under the same conditions except with 20 units of BamHI and 10 units of Acc65I per µg of DNA, phenol/chloroform extracted to remove restriction enzymes and recovered by ethanol precipitation. Ligation of the digested PCR fragments into the pUC19 vector was carried out using a 10:1 insert to vector ratio in a 20 µL volume containing 100 ng vector, with and without insert, and 400 units of T4 DNA ligase (New England Biolabs, Inc., Beverly, Mass.). Following overnight incubation at 16° C., 10 µL of each ligation (i.e. with and without insert) was heat-killed at 65° C. for 15 minutes and digested with SmaI to linearize any self-ligated vector. Digests (50 μL total) contained 10 μL ligation reaction and 20 units of SmaI in 1×NEBuffer 4 (20 mM Tris-acetate, pH 7.9, 50 mM potassium acetate, 10 mM magnesium acetate, 1 mM DTT) and were incubated at 20° C. for 3 hours. Following heat-killing at 65° C. for 15 minutes, a 1 μL aliquot of each digest was electroporated into *E. coli* ER2738 using a Bio-Rad Gene Pulser® (Bio-Rad, Hercules, Calif.) apparatus. Freshly electroporated cells were incubated in 1.0 ml of SOC media for 1 hour at 37° C. with shaking. Cells were plated on LB agar plates containing 100 μg/mL ampicillin and 40 μg/mL each of isopropyl-β-D-thiogalactopyranoside (IPTG) and 5-bromo-4-chloro-3-indolyl-β-D-galactopyranoside (X-gal), and incubated at 37° C. overnight. A mixture of blue and white colonies was observed, with the blue and white colony counts being 5-10 times and >20 times higher than the no insert control, respectively.

7. Sequencing and Analysis

DNA from a total of 126 clones was isolated from 1.5 mL cultures using QiaQuick® (Qiagen, Studio City, Calif.) spin columns, in a final volume of 50 μL. Restriction analysis and automated Sanger DNA sequencing (ABI 377 or 3100 instruments) indicated that 9 of the 126 sequenced clones contained no insert, while the remaining 117 clones had inserts corresponding to the two primer sequences (Primer 1 and Primer 2), with varying amounts of enclosed sequence between them corresponding to cloned RNA sequences (FIG. 4D). The length distribution for the cloned sequences was as follows (number of clones in parentheses): 13 bases (2), 14 bases (1), 15 bases (3), 16 bases (1), 17 bases (6), 18 bases (5), 19 bases (4), 20 bases (15), 21 bases (38), and 22 bases (38), 23 bases (1) and 24 bases (2). These sequences could be isolated from the primer sequences and matched to the transcribed portion of the parent Litmus-malE or GFP constructs (FIGS. 4B and 4C). The results definitively demonstrate that the cloned fragments span the entire duplex RNA starting material, and contain a substantial portion of the large dsRNA sequence indicating that RNaseIII digestion is random. Arrows correspond to sequences cloned as shown in FIGS. 4B and 4C; the direction of the arrowhead indicates whether the sequence corresponds to the sequence shown (left to right) or the complementary strand (right to left).

DNA inserts from individual clones carrying RNaseIII digestion generated fragments according to the scheme in FIG. 4A were isolated and sequenced. Insert length was determined by counting the number of remaining nucleotides in the fragment after identifying the primers used in the cloning method. A total of 126 inserts from two different transcripts (malE in Litmus 28i and gfp in Litmus 38i) were then plotted by insert length vs. frequency of occurrence and shown in the graph and table of FIG. 4D.

As shown in the table in FIG. 4D, 65% or 76 out of 117 insert containing clones had inserts either 21 or 22 nucleotides in length. 1 out of these 117 clones had an insert 5 nt in length i.e. shorter than 11 nt which is the size typically generated using prior art conditions for RnaseIII digestion in buffer containing $Mg^{2+}$ instead of $Mn^{2+}$. The above cloning experiment is further confirmation that a substantial fraction of the fragments generated by RNaseIII digestion in buffer containing $Mn^{2+}$ is 21-22 nt.

Example V

Generation of a Library of Cloned RNaseIII Products (a) A library of clones may be generated by cloning multiple cDNAs in Litmus28i, Litmus38i (New England Biolabs, Inc., Beverly, Mass.), or other opposing T7 promoter vector, after PCR amplification of the individual fragments or by using commercially available cDNA fragments. The library clones are used for the generation of dsRNA corresponding to each cloned sequence by in vitro transcription with T7 polymerase and subsequent cleavage with RNaseIII as described in the previous Examples.

(b) The RNAseIII digestion products of a large dsRNA, obtained and purified as described above or in Example IV can be cloned in a in a Litmus 28i vector as described in Example IV. Each clone now represents a single short sequence produced by RNaseIII cleavage of the original long sequence and can be used for the generation of a single short sequence segment dsRNA (for example, 18-25 bp) by in vitro transcription. Testing of multiple clones for effectiveness can be achieved in a high throughput format since all procedures (PCR, in vitro transcription, RNaseIII cleavage and transfection) can be performed in microtiter plate format with standardized methods. The best segments (most effective in silencing) are thus identified and can be introduced to specialized vectors (hairpin, adenoviral/retroviral) or chemically synthesized for specific downstream applications.

The short dsRNA products may be used in cell transfection assays or in transgenic animal studies for gene knock-outs of the cognate sequences. Suitable assays are performed to assess the silencing effects such as, cell morphology, viability, co-transfected reporter expression, susceptibility to drug treatments etc. All these procedures are amenable to automation in microtiter plate format.

Example VI

HsiRNA Mixtures are Effective in Gene Silencing of Transfected and Endogenous Genes in Insect or Mammalian Cells To test the effectiveness in inhibiting gene expression using hsiRNA produced by RNaseIII in the presence of a divalent transition metal cation buffer, long dsRNA preparations were synthesized by run-off transcription of firefly GL3 luciferase cDNA (F-Luc) (1.2 kb), green fluorescent protein (GFP) cDNA (0.8 kb), p53 cDNA (1.1 kb), and PKR cDNA (0.4 kb) using the HiScribe™ kit (New England Biolabs, Inc., Beverly, Mass.) and standard recombinant DNA techniques as instructed in the kit manuals and references provided by New England Biolabs, Inc. (Beverly, Mass.). The dsRNAs were phenol-extracted, and ethanol precipitated.

10 μg each of GFP dsRNA and F-Luc dsRNA were digested in 100 μl of 50 mM NaCl, 50 mM Tris-HCl, pH 7.5, 1 mM dithiothreitol supplemented with 10 mM $MnCl_2$ or 10 mM $MgCl_2$ and RNaseIII (20 μg) for 30 min at 37° C. The digestion products were ethanol precipitated and the pellet dissolved in sterile TE (10 mM Tris-HCl pH 7.5, 1 mM EDTA). The effectiveness of these RNaseIII-generated dsRNAs to reduce or eliminate the expression of luciferase, GFP or p53 were tested in (a) cultured *Drosophila* Schneider SL2 cultured cells, (b) Human Embryonic Kidney 293 cells, or (c) monkey epithelial Cos-7 cells. All cultures were in 24-well plates with 0.5 mL of the appropriate medium.

(a) *Drosophila* Schneider SL2 cultured cells were cultured in Schneider's medium supplemented by 10% fetal calf serum at 27° C. The cells were plated for transfection at $0.2×10^6$/ml/well of a 24-well plate 16 hours before transfection. A mixture consisting of 0.1 μg pGL2-based luciferase reporter plasmid, 0.05 μg Renilla luciferase reporter plasmid and 0.05-0.5 μg typically 0.1 μg GL3 luciferase dsRNA undigested or digested with RNaseIII as described above was mixed with 3 μL Cellfectin (Invitrogen, Carlsbad, Calif.) transfection reagent in 100 μL Schneider's medium without serum, incubated for 30 minutes at room temperature and added to one well of the transfection plate. After 40 hrs at 27° C. the cells were analyzed for luciferase activity using the dual luciferase reporter system (Promega, Madison, Wis.) as described in the dual luciferase manual. The relative luciferase activity was expressed as the ratio of Firefly luciferase to Renilla luciferase (FIG. 5).

(b) Human embryonic kidney cells (HEK-293) were cultured in Dulbecco's Modified Eagle Medium (DMEM) supplemented by 10% fetal calf serum at 37° C., 5% $CO_2$. The cells were plated for transfection at $0.2 \times 10^6$/well of a 6-well plate 16 hours before transfection. A mixture consisting of 0.1 μg pGL3-based luciferase reporter plasmid, 0.1 μg pEGFP and 0.05 μg Renilla luciferase reporter plasmid and 0.1-0.5 μg (typically 0.1 μg) hsiRNA (dsRNA digested with RNaseIII as described above) or 10 picomol of GFP-22 siRNA ((sense strand) 5'GCAAGCUGACCCUGAAGUUCAU3'. (SEQ ID NO:7) and (anti-sense strand) 5'GAACUUCAGGGU-CAGCUUGCCG (SEQ ID NO:8)) (Xeragon; Huntsville, Ala.) was mixed with 6 μL CELLFECTIN® (Invitrogen, Carlsbad, Calif.) transfection reagent in 150 μL DMEM without serum, incubated for 30 minutes at room temperature and added to one well of the transfection plate. The expression of GFP and luciferase were assessed by fluorescence and luminescence, respectively (FIG. 6A and FIG. 6B). For more efficient transfection luciferase hsiRNA (0.025 μg-14 nM final concentration) prepared as described above or GL3 luciferase hsiRNA (20 pmol) ((sense strand) 5'CUUACGCUGAGUACUUCGATT3' (SEQ ID NO:9) and (antisense strand) 5'UCGAAGUACUCAGCGUAAGTT (SEQ ID NO:10)) (Xeragon, Huntsville, Ala.) was transfected into HEK293 cells using Lipofectamine 2000 and OPTIMEM medium (Invitrogen, Carlsbad, Calif.)) using 2 μL Lipofectamine 2000 and 100 μL OPTIMEM (Invitrogen, Carlsbad, Calif.) for 1 well of a 24 well plate. The cells were processed for luciferase assays with the dual luciferase kit (Promega, Madison, Wis.) as instructed by the manufacturer (FIG. 6C).

(c) Monkey epithelial cells (COS-7) were cultured in Dulbecco's Modified Eagle Medium (DMEM) supplemented by 5% fetal calf serum at 37° C., 5% $CO_2$. The cells were plated for transfection at $0.2 \times 10^6$/0.5 mls in each well of a 24-well plate 24 hours before transfection or at 85% confluency 6 hrs before transfection. For each cell well a mixture consisting of 0.1 μg pEGFP and 1 or 5 μL hsiRNA (6 ng/μL) generated from larger dsRNA and purified by ethanol precipitation was mixed with 2 μL Lipofectamine 2000 transfection reagent (Invitrogen, Carlsbad, Calif.) in a final volume of 100 μL OPTIMEM (Invitrogen, Carlsbad, Calif.) as instructed by the manufacturer, incubated for 20 minutes at room temperature before addition to the cells. The expression of GFP was assessed by fluorescence microscopy, and the expression of other endogenous targets by Western blots of cell extracts with appropriate antibodies. In a separate experiment 0, 5 or 10 μL hsiRNA (5 ng/μL) produced from p53 dsRNA or 10 μL hsiRNA (5 ng/μL) produced from Renilla dsRNA as described above were used in a transfection along with a plasmid expressing a truncated form of human p53 (residues 100-393) in the pCDNA vector, and a plasmid expressing Renilla luciferase. The cells were lysed and processed for luciferase assays using the dual luciferase assay system (Promega, Madison, Wis.) 48 hrs post transfection. Lysates from individual wells were also analyzed by western blot using a polyclonal anti-p53 antibody (Cell Signaling Technologies, Beverly, Mass.). The test cells showed effective knock down of the expression of the target genes with efficiency comparable or better than that of chemically obtained siRNAs.

In FIG. 5, the long dsRNA corresponding to luciferase was shown to be effective in silencing activity in Drosophila cultured cells. HsiRNA mixtures appear to have the structure of a 2-base free 3'-OH overhang shown previously to be essential for achieving gene-silencing via the RNAi mechanism (Elbashir, et al., EMBO J., 20:6877-6888 (2001)). The products resulting from RNaseIII digestion in the presence of $Mg^{2+}$ only, however, were not able to effect silencing of luciferase. In contrast, RNAseIII digestion products in the presence of manganese ions were very effective in silencing. These results correlated with the size distribution of fragments generated by RNaseIII as shown in Examples IA and IB, demonstrate that the hsiRNA mixtures contains molecules that are of the proper size and sequence to trigger gene silencing.

A chemically synthesized siRNA corresponding to the pGL3 luciferase gene was found to be ineffective in this assay presumably because of point mutation differences in the corresponding sequence of pGL2/pGL3 luciferases. This result demonstrates the effectiveness of silencing using a mixture of double-stranded short RNAs as compared to a single molecule.

In FIG. 6A, the digestion products of GFP dsRNA in the presence of $Mn^{2+}$ are shown to be effective in specific silencing of GFP in mammalian cells as indicated by the absence of fluorescent cells compared to the non-treated control cells. The specificity of silencing and the absence of unwanted non-specific global effects is demonstrated in FIG. 6B where the activity of non-targeted luciferase is unaffected by the GFP dsRNA obtained in the presence of $Mn^{2+}$. FIG. 6C shows that silencing of luciferase by hsiRNA produced by RNaseIII is very effective, as compared to that obtained by 40 nM GL3 luciferase siRNA.

FIG. 7 shows that a concentration of hsiRNA fragments equal to 6 ng per one well of a 24 well plate is sufficient to cause significant silencing as detected by the decreased number of fluorescent cells. 30 ng showed dramatic knock-down of the GFP target gene expression with very high efficiency, whereas GFP is unaffected when equivalent amounts of hsiRNA fragments corresponding to an unrelated sequence were used.

In FIG. 8A the knock-down of both endogenous (E) and transfected (T) p53 by a hsiRNA mixture targeting p53 is detectable by the decrease or absence of the corresponding protein band (compare lanes 2 and 3 with lane 1). Conversely the Renilla luciferase activity is affected only in the case where the hsiRNA mixture targeting Renilla luciferase was used (FIG. 6B compare sample 1 to samples 2 and 3). In all cases tested the hsiRNA-treated cells showed effective knock-down of the expression of the target genes with efficiency comparable or better than that of chemically obtained siRNAs.

These results demonstrate that hsiRNA mixtures produced by RNaseIII in the presence of $Mn^{2+}$ ions is a potent and specific mediator of silencing for both transfected and endogenous genes and can be used to modulate gene expression in mammalian cells.

Example VII

Kits for Generating hsiRNA and for Gene Silencing in Mammalian Cells

A kit is provided for in vitro generation of hsiRNA mixtures and optionally for transfection of RNA fragments into mammalian cells.

In an embodiment of the invention, each kit contains reagents for processing multiple large dsRNAs for transfections in a 24-well plate format (sufficient for 100 transfections) and includes instructions for use.

Kit Components

The kit may contain enzyme and at least one of vectors, primers and buffers. Examples of components in a kit, all of which are individually available from New England Biolabs, Inc. (Beverly, Mass.), are listed below.

| | |
|---|---|
| T7 RNA Polymerase, 150 units/µl, | 25 µl |
| 10X Buffer/NTPs (see formulation below) | 60 µl |
| 30X High Molecular Weight Component Mix (HMW) (see formulation below) | 20 µl |
| BT7-minimal Primer (19 MER), 5'-Biotin-dCTCGAGTAATACGACTCACTATAG-3', (SEQ ID NO: 11) (10 µM) | 25 µL |
| 10X Ribonuclease III (1.4 µg/µl) | 100 µL |
| 10X hsiRNA Buffer (see formulation below) | |
| 10X MnCl$_2$ (200 mM) | 1000 µL |
| 10X EDTA (250 mM) | 1000 µL |
| Litmus 38iluc control template, | 1 µg |
| RNase-free glycogen 10 µg/µL | 50 µL |
| Plasmid DNA 500 µg/ml in TE buffer (10 mM Tris-HCl, pH 8.0, 1 mM EDTA) | |

In addition, the kit may include transfection reagents, RNA size markers and Streptavidin-coated beads.

| Buffer compositions |
|---|
| (a) 10X Buffer/NTPs:<br>400 mM Tris-HCl, pH 8.1<br>190 mM MgCl$_2$<br>50 mM DTT<br>10 mM spermidine<br>40 mM each NTP |
| (b) 30X High Molecular Weight (HMW) Mix:<br>20 mM Tris-HCl, pH 8.1<br>1.5 mg/ml BSA<br>100 units/ml inorganic pyrophosphatase (yeast)<br>12,000 units/ml pancreatic ribonuclease inhibitor<br>50% glycerol |
| (c) 10x hsiRNA buffer<br>0.5M Tris-HCl, pH 7.5<br>10 mM DTT |

The kit utilizes RNaseIII in an optimized buffer to produce fragments in the range of about 18-25 nucleotides from long dsRNA. The dsRNA product is cleaved with RNaseIII to reproducibly yield hsiRNA mixtures suitable for silencing gene expression. The sequences of different siRNA fragments in the mixture map to sequences along the entire target gene. The hsiRNA mixtures can be purified by ethanol precipitation and used in transfection.

In addition to RNaseIII, the kit may include reagents for high-yield in vitro transcription of large dsRNA from DNA templates flanked by T7 promoters along with instructions for use and optionally a reaction vessel for conducting the reactions.

An example of instructions accompanying the kit include the following:

(1) Cloning the DNA Template Prior to in vitro Transcription to Generate dsRNA

One approach to making a DNA template for transcription is to clone a DNA of interest in Litmus 28i/38i bi-directional transcription vectors (New England Biolabs, Inc., Beverly, Mass.). The DNA of interest can then be amplified by PCR using a single T7 promoter-specific primer such as a BT7 Minimal Primer which produces a linear product with the target sequence flanked by T7 promoters which define the ends.

Alternatively target gene-specific primers with appended T7 promoters can be used to amplify any specific cDNA sequences. For example, the amplification primer:

(SEQ ID NO: 12)
5' <u>TAATACGACTCACTATAG</u>aaggacagatggttaagtac-3'
    T7 promoter in which a T7 promoter (underlined) located at the 5' end preceding the target-specific sequence (bold) can be used for amplifying any cDNA template.

Biotinylated BT7 primer can be used to amplify any sequence flanked by T7 promoters. Optionally, the amplified biotinylated DNA template can be isolated by binding to streptavidin magnetic beads (New England Biolabs, Inc., Beverly, Mass.) and used directly as a template for transcription. For forming an immobilized DNA template, 25-50 µL of streptavidin magnetic bead suspension is added to the amplification (PCR) reaction mix with an equal volume of 1 M NaCl and incubate at room temperature for 10-15 minutes. The supernatant is removed in the presence of a magnet and the beads washed with 0.5 mLs TE, 0.5 M NaCl. The resuspended beads can be used directly in the transcription reaction. In vitro transcription of the immobilized DNA template produces DNA-free double-stranded RNA.

Amplification can be achieved by any polymerase dependent method such as PCR. The amplification product is purified by ethanol precipitation, or by a chromatographic method (e.g., QiaQuick® column (Qiagen, Studio City, Calif.)) and resuspended in TE (10 mM Tris-HCl, pH 8.0, 1 mM EDTA, prepared with Milli-Q water or equivalent) to a final concentration of ~500 µg/ml.

A control consisting of GL3 luciferase can be prepared using a Litmus 38iLuc plasmid in which a 1.0-kbp fragment of the GL3 luciferase gene is cloned in the SphI and NgoMIV sites of Litmus 38i. Linearization with MfeI and StuI (in separate reactions), followed by in vitro transcription of the combined linearized templates, produces double-stranded RNA 1.0 kbp in length.

Pilot studies can be undertaken for providing an hsiRNA mixture for specific gene silencing using one or more fragments obtained by cleaving double-stranded RNA having a length of 100-600 bp including RNA derived from restriction fragments of a cDNA which has been subcloned into Litmus28i/38i vectors (New England Biolabs, Inc., Beverly, Mass.).

In Vitro Transcription

In vitro transcription is performed using the DNA template prepared as described above. The volume of template used in the transcription reaction depends on the method of purification. For unpurified PCR product, no more than 5 µl is used per 30 µl reaction. The amount of added template DNA should not exceed 1 µg per 30 µl reaction.

| | |
|---|---|
| RNase-Free Water | 50-x µl |
| 10X Buffer/NTPs | 6 µl |
| DNA template (~0.5-1 µg) | x µl |
| 30X HMW Mix | 2 µl |
| T7 RNA Polymerase (150 U/µl) | 2 µl |
| | 60 µl |

Incubation at 42° C. can improve yields of RNA transcripts containing substantial secondary structure. As it is difficult to gauge the secondary structure content in a particular transcript, we recommend that all transcription be carried out at 42° C. if possible. Transcription yields increase linearly for the first 90 minutes (approximately) and reach maximum after 2-3 hours. Reactions can be carried out overnight if desired, but yields will not be higher. Double-stranded RNA is stable upon prolonged incubation at 37° C.

The transcription reaction can be analyzed on a 1% agarose gel taking care to avoid RNase contamination. Double-stranded RNA migrates approximately as the DNA template used in the reaction. The expected length of the transcript from the Litmus 38iluc control template is 1000 bp.

The double-stranded RNA transcription product is purified by ethanol precipitation. One-tenth volume of 3 M NaOAc is added at a pH 5.5 with 2 volumes of cold 95% ethanol. Incubate on ice for 15 minutes, or store at −20° C. overnight. Spin for 15 minutes in a microcentrifuge at 14,000 rpm. Remove supernatant, add two volumes 80% ethanol, incubate at room temperature for 10 minutes, centrifuge for 5 minutes, and decant and drain the tube. Allow the pellet to air-dry. Dissolve the dried RNA in 10 mM Tris-HCl, pH 8.0, 1 mM EDTA, or dH$_2$0.

Forming an hsiRNA Mixture

Use 1× (10-fold diluted) RNaseIII at a concentration of (0.14 ug/ul) and 0.07 µg/µL of dsRNA in the digestion reaction as in the following example.

Combine the following:

| | |
|---|---|
| dH$_2$O | 105-x µL |
| 10X hsiRNA Buffer | 15 µl |
| dsRNA | x µL (10 µg) |
| RNaseIII | 15 µl |
| 10X MnCl$_2$ | 15 µl |
| | 150 µl |

Incubate for 20 min at 37° C.

Promptly add 15 µl 10×EDTA to stop the reaction.

For monitoring the products of digestion, a 10-20% native polyacrylamide gel is suitable. The product of digestion reveals that the long dsRNA has been cleaved to yield an hsiRNA mixture of fragments having a size in the range of 18-25 nucleotides regardless of the length of the starting long dsRNA. The mixture can be purified by the single step of ethanol precipitation prior to use in transfection.

Ethanol Precipitation of hsiRNA Fragments.

Add one-tenth volume of 3 M NaOAc, pH 5.5, 2 µL glycogen solution and 3 volumes of cold 95% ethanol. Place at −70° C. for 30 minutes, or −20° C. for 2 hrs-overnight. Spin for 15 minutes in a microcentrifuge at 14,000 rpm. Remove supernatant carefully avoiding the small pellet, add two volumes 80% ethanol, incubate at room temperature for 10 minutes, centrifuge for 5 minutes, and decant and drain the tube. Allow the pellet to air-dry. Dissolve the dried RNA in 10 mM Tris-HCl, pH 8.0, 1 mM EDTA, or dH$_2$0.

Determining dsRNA Concentration:

This can be measured using a UV spectrophotometer (OD at 260 nm of 1 corresponds to 40 µg/mL dsRNA) or a fluorometer (using RIBOGREEN®, Molecular Probes, Eugene, Oreg.) or comparisons to siRNA standards used in the art.

Transfection Guidelines:

After ethanol precipitation, hsiRNA mixtures can be directly transfected into mammalian cells using reagents and protocols suitable for oligonucleotide transfections such as lipofectin 2000, oligofectamine, TRANS-IT TKO® (Mirus Corp., Madison, Wis.) and Targefect (Targeting Systems, Santee, Calif.). Additionally Calcium Phosphate and Electroporation have been reported to be efficient in transfecting short RNAs.

Amounts of 25-100 ng of hsiRNA can be used per transfection well (24-well format) as an initial amount to be adjusted according to experimental findings.

Large dsRNA may be synthesized by in vitro transcription as described above using a modified transcription buffer containing modified ribonucleotides such in place of NTPS in 10× buffer described above such as 2-fluoro-ribo-CTP, 2-fluoro-ribo-UTP, 2-O-methyl-ribo-CTP, 2-O-methyl-ribo-UTP, 2-O-methyl-ribo-ATP, 2-O-methyl-ribo-GTP or other 2' modifications that render the dsRNA more stable or resistant to degradation. A DURASCRIBE® kit (Epicentre Technologies, Madison, Wis.) may be used for these purposes.

Example VIII

HsiRNA Mixtures Corresponding to Different Sequence Segments of a Target mRNA are Effective in Silencing the Target mRNA The effectiveness of hsiRNA mixtures from large double-stranded RNAs which are complementary to different segments of a target gene for inhibiting gene expression was determined using mixtures produced by RNaseIII digestion in the presence of 10 mM Mn$^{2+}$ ions as described in Example VI. Large dsRNA preparations were synthesized by run-off transcription of 3 cDNA fragments of human DNA methyltransferase 1 (DnMt1) (Acc. X63692). Segment 1 corresponding to nucleotides (1737-2113), segment 2 corresponding to nucleotides (2114-3230), and segment 3 corresponding to nucleotides (3231-4391), were amplified by PCR and cloned into Litmus 28i. dsRNA was produced using the HiScribe™ kit (New England Biolabs, Inc., Beverly, Mass.) and standard recombinant DNA techniques as instructed in the kits manuals and references provided by New England Biolabs, Inc. (Beverly, Mass.). The dsRNAs were ethanol precipitated and processed with RNaseIII in the presence of 10 mM MnCl$_2$.

The effectiveness of these RNaseIII-generated hsiRNA mixtures to reduce the expression of DnMT1 was tested in monkey epithelial COS-7 cells. Cells were cultured as described in Example VI and transfected at 1 µg/well with an expression plasmid (pcDNA-4 containing the full length human DnMT1 sequence fused to a hexa-histidine tag) in the following formats: a: alone, or b: with 100 ng synthetic siRNA against luciferase, or c: with 100 ng hsiRNA from DnMT1 segment 1, or d: with 100 ng hsiRNA from DnMT1 segment 2 or e: with 100 ng hsiRNA from DnMT1 segment 3, using Lipofectamine 2000 as described in Example VI. The final concentration of hsiRNA was 15 nM. The cells were lysed at 48 hr after transfection and a fraction from each lysate was analyzed in a western blot by probing with anti-DnMT1 antibody (New England Biolabs, Inc., Beverly, Mass.) to determine specific silencing effects and anti-p53 antibody to test for non-specific silencing effects.

The results of the western blots (FIGS. 10A and 10B) show that all three segments produce hsiRNA effective in reducing the expression of DnMT1 but not affecting the expression of p53 (lanes 4, 5 and 6). The results also showed that the hsiRNA mixture from segment 2 (lane 6) was more potent in silencing than those from the other two segments as indicated by the diminished signal for the corresponding band on the Western Blot when compared with the products obtained from the other segments.

Example IX

A Method for Discovering Effective siRNA Sequences Using Large dsRNA Digested with an RNaseIII

Determination of Single Active siRNAs Against DnMT1

The hsiRNA mixture corresponding to fragment 2 of human DNA methyl-transferase 1 (DnMt1, ACC. X63692). nucleotides (2114-3230) at a concentration of 200 ng/mL is introduced into HEK293 cells using Lipofectamine 2000 to induce RNAi-mediated silencing of the DnMT1 mRNA as described in Example VIII. Total RNA from the treated cells and for control cells treated with an hsiRNA mixture directed at a non-target gene eg GFP is first extracted 6 hr after transfection using RNAwiz reagent (Ambion, Austin, Tex.) and then used for isolation of mRNA using poly-A-spin kit (New England Biolabs, Inc., Beverly, Mass.) according to manufactures' protocols. DNA antisense:

primer 1: (gtcagtctcattgggcctgccgtt) (SEQ ID NO:13), primer 2: (gaaggcctcagggggcaggtacaca) (SEQ ID NO:14), primer 3: (tcataccacagctggtagaagtaggt) (SEQ ID NO:15)

are synthesized using standard synthesis and labeled at the 5' end with alpha 32P-ATP and polynucleotide kinase (PNK), (New England Biolabs, Inc., Beverly, Mass.) at high specific activity using the protocols provided by the manufacturer.

Primer extension is performed in two sets of three separate reactions. One set is using RNA from cells treated with the hsiRNA mixture and the second from negative control cells which were treated with siRNA directed towards GFP. Each primer extension reaction is performed with 1 µg of A+-RNA and the Promega Primer Extension System (Promega, Madison, Wis.) according to the manufacturer's guidelines and standard protocols described in Molecular Cloning Manual (Sambrook et al. (2001)). The primer extension products are analyzed in a polyacrylamide sequencing gel next to Sanger sequencing ladders prepared with primers 1, 2 and 3 and the Litmus construct of fragment 2 as the DNA template, to allow identification of the products at single nucleotide resolution. The cleavage sites on the target DNMT1 RNA are identified by comparing the mobility of the primer extension product bands to those that co-migrate in the respective sequencing ladders e.g., extension products of primer 1 are compared to sequencing ladders generated with primer 1. The protocol described above is summarized in FIG. 11. The results provide a sequence for the mRNA at the cleavage site. With the knowledge that the siRNA binds to mRNA in such a way as to cause cleavage at a site corresponding to the central region of the siRNA (Martinez et al. Cell 110:563-574 (2002)), it is possible to determine the sequence of the full length siRNA fragment responsible for the identified cleavage of mRNA from the sequence at the cleavage site. Once the sequence of the siRNA fragment responsible for cleavage is identified, DNA having the identified sequence can be made and clones prepared using standard techniques of inserting DNA into a vector having promoters that capable of expressing double-stranded RNA. The cloned DNA encoding the siRNA may then serve as a reagent for studying gene silencing or for use as a therapeutic agent.

In addition to the above, a cloned DNA encoding the siRNA sequence may be cloned. This DNA will express an RNA that has a hairpin structure. The DNA serves as a reagent for gene silencing. Alternatively, DNA may be chemically synthesized for use in vitro transcription. In these circumstances, the sequence of the desired siRNA is synthesized in the form of DNA having a repeat sequence in which a spacer is inserted. Once transcribed, the RNA repeats which are in opposing orientation can generate hairpin products with the loop region represented by the spacer. (Milligan, et al., *Nucleic Acids Res.*, 15:8783-8798 (1987)).

What is claimed is:

1. A method of producing a plurality of overlapping double stranded (ds) RNA fragments of a size in the range of about 15-30 nucleotides, comprising:
   (a) digesting a preparation of large double-stranded RNA in a reaction mixture containing a divalent transition metal cation and a prokaryotic RNaseIII wherein the ratio of enzyme to substrate (w/w) is greater than or equal to about 0.25:1; and
   (b) producing the plurality of overlapping dsRNA fragments of a size in the range of about 15-30 nucleotides.

2. A method according to claim 1, wherein the plurality of overlapping fragments is the product of complete digestion of the preparation of large double-stranded RNA.

3. A method according to claim 1, wherein the transition metal cation is manganese.

4. A method according to claim 3, wherein the reaction mixture contains manganese ions at a concentration in the range of about 5-10 mM.

5. A method according to claim 3, wherein the reaction mixture contains manganese ions at a concentration in the range of about 10-20 mM.

6. A method according to claim 1, wherein the transition metal is selected from nickel, cobalt and cadmium.

7. A method according to claim 2, wherein the complete digestion is achieved in less than 6 hours.

8. A method according to claim 2, wherein the complete digestion—is achieved in less than 2 hours.

9. A method of silencing expression of a target gene, comprising:
introducing into a host cell, a plurality of fragments made according to claim 1, wherein the nucleotide sequence for each fragment has a sequence that is complementary to the target gene.

10. A purified set of double-stranded RNA fragments, comprising a plurality of overlapping fragments of a size in the range of about 15-30 nucleotides, the fragments in the set collectively representing a substantial portion of a sequence of one or more large double-stranded RNAs from which the fragments are derived by in vitro cleavage with a purified enzyme, one strand of each of the large double-stranded RNA having a sequence complementary to part or all of a target RNA.

11. A set of fragments according to claim 10, wherein the substantial portion is greater than about 50% of the sequence of the large double-stranded RNA.

12. A set of fragments according to claim 10, wherein the substantial portion is greater than about 65% of the sequence of the large double-stranded RNA.

13. A set of fragments according to claim 10, wherein more than about 30% of the RNA fragments have a fragment size of about 18-25 base pairs.

14. A set of fragments according to claim 10, wherein at least one fragment and as many as 100% of fragments in the set are capable of causing cleaving the target RNA in a cell.

15. A set of fragments according to claim 14, wherein at least about 50% of the fragments are capable of causing cleavage of the RNA.

16. A set of fragments according to claim 14, wherein at least about 75% of the fragments are capable of causing cleavage of the mRNA.

17. A set of fragments according to claim 10, capable of RNA silencing in vivo when introduced into a eukaryotic cell.

18. A purified set of double-stranded RNA fragments according to claim 10, wherein the fragments bind specifically to mRNA to initiate cleavage of the mRNA.

* * * * *

SEQUENCE LISTING

```
<160> NUMBER OF SEQ ID NOS: 15

<210> SEQ ID NO 1
<211> LENGTH: 908
<212> TYPE: DNA
<213> ORGANISM: unknown
<220> FEATURE:
<223> OTHER INFORMATION: malE transcript

<400> SEQUENCE: 1
gggcagatct gctgccgaac ccgccaaaaa cctgggaaga gatcccggcg ctggataaag      60
aactgaaagc gaaaggtaag agcgcgctga tgttcaacct gcaagaaccg tacttcacct     120
ggccgctgat tgctgctgac gggggttatg cgttcaagta tgaaaacggc aagtacgaca     180
ttaaagacgt gggcgtggat aacgctggcg cgaaagcggg tctgaccttc ctggttgacc     240
tgattaaaaa caaacacatg aatgcagaca ccgattactc catcgcagaa gctgccttta     300
```

| | |
|---|---|
| ataaaggcga acagcgatg accatcaacg gcccgtgggc atggtccaac atcgacacca | 360 |
| gcaaagtgaa ttatggtgta acggtactgc cgaccttcaa gggtcaacca tccaaaccgt | 420 |
| tcgttggcgt gctgagcgca ggtattaacg ccgccagtcc gaacaaagag ctggcaaaag | 480 |
| agttcctcga aaactatctg ctgactgatg aaggtctgga agcggttaat aaagacaaac | 540 |
| cgctgggtgc cgtagcgctg aagtcttacg aggaagagtt ggcgaaagat ccacgtattg | 600 |
| ccgccactat ggaaaacgcc cagaaaggtg aaatcatgcc gaacatcccg cagatgtccg | 660 |
| ctttctggta tgccgtgcgt actgcggtga tcaacgccgc cagcggtcgt cagactgtcg | 720 |
| atgaagccct gaaagacgcg cagactaatt cgagctcgaa caacaacaac aataacaata | 780 |
| acaacaacct cgggatcgag ggaaggattt cagaattcct gcaggatatc tggatccacg | 840 |
| aagcttccca tggtgacgtc accggttcta gatacctagg tgagctctgg taccctctag | 900 |
| tcaaggcc | 908 |

<210> SEQ ID NO 2
<211> LENGTH: 868
<212> TYPE: DNA
<213> ORGANISM: unknown
<220> FEATURE:
<223> OTHER INFORMATION: Green Fluorescent Protein transcript

<400> SEQUENCE: 2

| | |
|---|---|
| taatacgact cactataggg gcccgtgcaa ttgaagccgg ctggcgccaa gcttctctgc | 60 |
| aggatatctg gatccacgaa ttcgctagcc taccggtcgc caccatggtg agcaagggcg | 120 |
| aggagctgtt caccggggtg gtgcccatcc tggtcgagct ggacggcgac gtaaacggcc | 180 |
| acaagttcag cgtgtccggc gagggcgagg gcgatgccac ctacggcaag ctgaccctga | 240 |
| agttcatctg caccaccggc aagctgcccg tgccctggcc caccctcgtg accaccctga | 300 |
| cctacggcgt gcagtgcttc agccgctacc ccgaccacat gaagcagcac gacttcttca | 360 |
| agtccgccat gcccgaaggc tacgtccagg agcgcaccat cttcttcaag gacgacggca | 420 |
| actacaagac ccgcgccgag gtgaagttcg agggcgacac cctggtgaac cgcatcgagc | 480 |
| tgaagggcat cgacttcaag gaggacggca acatcctggg gcacaagctg gagtacaact | 540 |
| acaacagcca caacgtctat atcatggccg acaagcagaa gaacggcatc aaggtgaact | 600 |
| tcaagatccg ccacaacatc gaggacggca gcgtgcagct cgccgaccac taccagcaga | 660 |
| acacccccat cggcgacggc cccgtgctgc tgcccgacaa ccactacctg agcacccagt | 720 |
| ccgccctgag caaagacccc aacgagaagc gcgatcacat ggtcctgctg gagttcgtga | 780 |
| ccgccgccgg gatcactctc ggcatggacg agctgtacag gcatgcgtcg accctctagt | 840 |
| caaggcctat agtgagtcgt attacgga | 868 |

<210> SEQ ID NO 3
<211> LENGTH: 18
<212> TYPE: DNA
<213> ORGANISM: unknown
<220> FEATURE:
<223> OTHER INFORMATION: primer

<400> SEQUENCE: 3

| | |
|---|---|
| taaacgactc actatagg | 18 |

<210> SEQ ID NO 4
<211> LENGTH: 21
<212> TYPE: DNA

```
<213> ORGANISM: unknown
<220> FEATURE:
<223> OTHER INFORMATION: primer

<400> SEQUENCE: 4
ctgcaggata tctggatcca c                                              21

<210> SEQ ID NO 5
<211> LENGTH: 25
<212> TYPE: DNA
<213> ORGANISM: unknown
<220> FEATURE:
<223> OTHER INFORMATION: primer

<400> SEQUENCE: 5
catgcccggg tacctttcta ttctc                                          25

<210> SEQ ID NO 6
<211> LENGTH: 21
<212> TYPE: DNA
<213> ORGANISM: unknown
<220> FEATURE:
<223> OTHER INFORMATION: primer

<400> SEQUENCE: 6
gtggatccag atatcctgca g                                              21

<210> SEQ ID NO 7
<211> LENGTH: 22
<212> TYPE: RNA
<213> ORGANISM: unknown
<220> FEATURE:
<223> OTHER INFORMATION: sense strand Green Fluorescent Protein siRNA

<400> SEQUENCE: 7
gcaagcugac ccugaaguuc au                                             22

<210> SEQ ID NO 8
<211> LENGTH: 22
<212> TYPE: RNA
<213> ORGANISM: unknown
<220> FEATURE:
<223> OTHER INFORMATION: antisense Green Fluorescent Protein siRNA

<400> SEQUENCE: 8
gaacuucagg gucagcuugc cg                                             22

<210> SEQ ID NO 9
<211> LENGTH: 21
<212> TYPE: DNA
<213> ORGANISM: unknown
<220> FEATURE:
<223> OTHER INFORMATION: sense strand luciferase GL3 siRNA

<400> SEQUENCE: 9
cuuacgcuga guacuucgat t                                              21

<210> SEQ ID NO 10
<211> LENGTH: 21
<212> TYPE: DNA
<213> ORGANISM: unknown
<220> FEATURE:
<223> OTHER INFORMATION: antisense strand luciferase GL3 siRNA

<400> SEQUENCE: 10
ucgaaguacu cagcguaagt t                                              21
```

```
<210> SEQ ID NO 11
<211> LENGTH: 24
<212> TYPE: DNA
<213> ORGANISM: unknown
<220> FEATURE:
<223> OTHER INFORMATION: primer

<400> SEQUENCE: 11
ctcgagtaat acgactcact atag                                          24

<210> SEQ ID NO 12
<211> LENGTH: 38
<212> TYPE: DNA
<213> ORGANISM: unknown
<220> FEATURE:
<223> OTHER INFORMATION: amplification primer

<400> SEQUENCE: 12
taatacgact cactatagaa ggacagatgg ttaagtac                            38

<210> SEQ ID NO 13
<211> LENGTH: 24
<212> TYPE: DNA
<213> ORGANISM: unknown
<220> FEATURE:
<223> OTHER INFORMATION: DNA antisense primer 1

<400> SEQUENCE: 13
gtcagtctca ttgggcctgc cgtt                                          24

<210> SEQ ID NO 14
<211> LENGTH: 25
<212> TYPE: DNA
<213> ORGANISM: unknown
<220> FEATURE:
<223> OTHER INFORMATION: DNA antisense primer 2

<400> SEQUENCE: 14
gaaggcctca gggggcaggt acaca                                         25

<210> SEQ ID NO 15
<211> LENGTH: 26
<212> TYPE: DNA
<213> ORGANISM: unknown
<220> FEATURE:
<223> OTHER INFORMATION: DNA antisense primer 3

<400> SEQUENCE: 15
tcataccaca gctggtagaa gtaggt                                        26
```